United States Patent
Günther et al.

(10) Patent No.: US 11,723,861 B2
(45) Date of Patent: Aug. 15, 2023

(54) OPHTHALMIC COMPOSITIONS COMPRISING LATANOPROST FOR USE IN THE TREATMENT OF OCULAR DISEASES

(71) Applicant: NOVALIQ GMBH, Heidelberg (DE)

(72) Inventors: Bernhard Günther, Dossenheim (DE); Frank Löscher, Schriesheim (DE); Kirsten Eickhoff, Heidelberg (DE)

(73) Assignee: NOVALIQ GMBH, Heidelberg (DE)

( * ) Notice: Subject to any disclaimer, the term of this patent is extended or adjusted under 35 U.S.C. 154(b) by 227 days.

(21) Appl. No.: 16/651,298

(22) PCT Filed: Sep. 25, 2018

(86) PCT No.: PCT/EP2018/075974
§ 371 (c)(1),
(2) Date: Mar. 26, 2020

(87) PCT Pub. No.: WO2019/063551
PCT Pub. Date: Apr. 4, 2019

(65) Prior Publication Data
US 2020/0268648 A1    Aug. 27, 2020

(30) Foreign Application Priority Data
Sep. 27, 2017  (EP) .................................... 17193364

(51) Int. Cl.
*A61K 31/5575*  (2006.01)
*A61K 9/08*  (2006.01)
(Continued)

(52) U.S. Cl.
CPC .............. *A61K 9/0048* (2013.01); *A61K 9/08* (2013.01); *A61K 31/5575* (2013.01); *A61K 47/06* (2013.01)

(58) Field of Classification Search
CPC ......................... A61K 31/5575; A61K 9/0048
See application file for complete search history.

(56) References Cited

U.S. PATENT DOCUMENTS

| 2,616,927 A | 11/1952 | Kauck et al. |
| 4,452,818 A | 6/1984 | Haidt |
(Continued)

FOREIGN PATENT DOCUMENTS

| CN | 1147213 A | 4/1997 |
| CN | 200977281 | 11/2007 |
(Continued)

OTHER PUBLICATIONS

Anonymous, "Semifluorinated alkane technology brings advantages for topical therapy,"Ophthalmology Times, pp. 1-2 (2016) http://www.ophthalmologytimes.com/ophthalmology/semifluorinated-alkane-technology-brings-advantages-topical-therapy.
(Continued)

*Primary Examiner* — Craig D Ricci
*Assistant Examiner* — Janet L Coppins
(74) *Attorney, Agent, or Firm* — Hoxie & Associates LLC

(57) ABSTRACT

The invention provides a pharmaceutical composition for use in the prevention or therapy of glaucoma, increased intraocular pressure, ocular hypertension and/or a symptom associated therewith, wherein—the composition comprises latanoprost and a liquid vehicle comprising a semifluorinated alkane; and—the composition is administered to the eye of a subject; and—the amount of latanoprost administered in a single dose per eye is in the range of from about 0.5 to 1.4 µg.

13 Claims, 2 Drawing Sheets

(51) Int. Cl.
*A61K 9/00* (2006.01)
*A61K 47/06* (2006.01)

(56) References Cited

U.S. PATENT DOCUMENTS

| | | | |
|---|---|---|---|
| 5,077,036 A | 12/1991 | Long, Jr. |
| 5,152,997 A | 10/1992 | Elbert et al. |
| 5,254,338 A | 10/1993 | Sakai et al. |
| 5,326,566 A | 7/1994 | Parab |
| 5,336,175 A | 8/1994 | Mames |
| 5,370,313 A | 12/1994 | Beard |
| 5,518,731 A | 5/1996 | Meadows |
| 5,667,809 A | 9/1997 | Trevino |
| 5,851,544 A | 12/1998 | Penska et al. |
| 5,874,469 A | 2/1999 | Maniar et al. |
| 5,874,481 A | 2/1999 | Weers |
| 5,904,933 A | 5/1999 | Riess et al. |
| 5,980,936 A | 11/1999 | Krafft et al. |
| 5,981,607 A | 11/1999 | Ding |
| 6,042,845 A | 3/2000 | Sun et al. |
| 6,060,085 A | 5/2000 | Osborne |
| 6,113,919 A | 9/2000 | Cronelus |
| 6,140,374 A | 10/2000 | May et al. |
| 6,159,977 A | 12/2000 | Reeves |
| 6,177,477 B1 | 1/2001 | George et al. |
| 6,197,323 B1 | 3/2001 | Georgieff |
| 6,224,887 B1 | 5/2001 | Samour et al. |
| 6,262,126 B1 | 7/2001 | Meinert |
| 6,264,990 B1 | 7/2001 | Knepp et al. |
| 6,294,563 B1 | 9/2001 | Garst |
| 6,335,335 B2 | 1/2002 | Higashiyama |
| 6,372,243 B2 | 4/2002 | Kobuch et al. |
| 6,391,879 B1 | 5/2002 | Reeves |
| 6,399,087 B1 | 6/2002 | Zhang et al. |
| 6,458,376 B1 | 10/2002 | Meadows |
| 6,486,212 B2 | 11/2002 | Meinert |
| 6,489,367 B1 | 12/2002 | Meinert |
| 6,528,086 B2 | 3/2003 | Zhang |
| 6,576,663 B2 | 6/2003 | Klimko |
| 6,730,328 B2 | 5/2004 | Maskiewicz |
| 7,001,607 B1 | 2/2006 | Menz |
| 7,026,359 B2 | 4/2006 | Gross |
| 7,258,869 B1 | 8/2007 | Berry |
| 7,687,445 B2 | 3/2010 | Bonnet et al. |
| 7,740,875 B2 | 6/2010 | Dechow |
| 7,776,349 B2 | 8/2010 | Dechow et al. |
| 8,029,977 B2 | 10/2011 | Meinert et al. |
| 8,222,292 B2 | 7/2012 | Goskonda et al. |
| 8,470,873 B2 | 6/2013 | Chen |
| 8,492,334 B2 | 7/2013 | Lavik et al. |
| 8,614,178 B2 | 12/2013 | Theisinger et al. |
| 8,759,404 B2 | 6/2014 | Daftary et al. |
| 8,796,340 B2 | 8/2014 | Theisinger et al. |
| 8,916,157 B2 | 12/2014 | Krause et al. |
| 8,986,738 B2 | 3/2015 | Meinert |
| 9,241,900 B2 | 1/2016 | Wilson |
| 9,308,262 B2 | 4/2016 | Wilson |
| 9,757,459 B2 | 9/2017 | Theisinger et al. |
| 9,757,460 B2 | 9/2017 | Günther et al. |
| 9,770,508 B2 | 9/2017 | Günther et al. |
| 10,045,996 B2 | 8/2018 | Theisinger et al. |
| 10,045,997 B2 | 8/2018 | Chen et al. |
| 10,058,615 B2 | 8/2018 | Günther et al. |
| 10,064,944 B2 | 9/2018 | Wilson |
| 10,130,707 B2 | 11/2018 | Günther et al. |
| 10,369,117 B2 | 8/2019 | Günther et al. |
| 10,449,164 B2 | 10/2019 | Günther et al. |
| 10,507,132 B2 | 12/2019 | Graf et al. |
| 10,525,062 B2 | 1/2020 | Theisinger et al. |
| 10,555,953 B2 | 2/2020 | Theisinger et al. |
| 10,576,154 B2 | 3/2020 | Günther et al. |
| 10,682,315 B2 | 6/2020 | Scherer et al. |
| 10,813,976 B2 | 10/2020 | Löscher et al. |
| 11,154,513 B2 | 10/2021 | Scherer et al. |
| 11,160,865 B2 | 11/2021 | Theisinger et al. |
| 2002/0004063 A1 | 1/2002 | Zhang |
| 2002/0006442 A1 | 1/2002 | Mishra et al. |
| 2002/0128527 A1 | 9/2002 | Meinert |
| 2002/0137793 A1 | 9/2002 | Klimko |
| 2003/0018044 A1 | 1/2003 | Peyman |
| 2003/0027833 A1 | 2/2003 | Cleary et al. |
| 2003/0170194 A1 | 11/2003 | Piotrowiak |
| 2004/0044045 A1 | 3/2004 | Burk |
| 2004/0082660 A1 | 4/2004 | Ueno |
| 2004/0101551 A1 | 5/2004 | Selzer |
| 2004/0265362 A1 | 12/2004 | Susilo |
| 2004/0266702 A1 | 12/2004 | Dawson |
| 2005/0075407 A1 | 4/2005 | Dov et al. |
| 2005/0079210 A1 | 4/2005 | Gupta |
| 2005/0175541 A1 | 8/2005 | Lanza et al. |
| 2005/0274744 A1 | 12/2005 | Spada et al. |
| 2005/0288196 A1 | 12/2005 | Horn |
| 2006/0153905 A1 | 7/2006 | Carrara et al. |
| 2007/0238732 A1 | 10/2007 | Graham et al. |
| 2008/0019926 A1 | 1/2008 | Krafft et al. |
| 2008/0050335 A1 | 2/2008 | Faour et al. |
| 2008/0153909 A1 | 6/2008 | Dana et al. |
| 2008/0207537 A1 | 8/2008 | Turner et al. |
| 2008/0234389 A1 | 9/2008 | Mecozzi et al. |
| 2008/0260656 A1 | 10/2008 | Mallard |
| 2009/0136430 A1 | 5/2009 | Dugger |
| 2009/0149546 A1 | 6/2009 | Chang |
| 2009/0169601 A1 | 7/2009 | Koch et al. |
| 2010/0006600 A1 | 1/2010 | Dascanio |
| 2010/0008996 A1 | 1/2010 | Meinert |
| 2010/0016814 A1 | 1/2010 | Gokhale et al. |
| 2010/0137252 A1 | 6/2010 | Matsumura et al. |
| 2010/0226997 A1 | 9/2010 | Bowman et al. |
| 2010/0274215 A1 | 10/2010 | Wong et al. |
| 2010/0310476 A1 | 12/2010 | Tamarkin et al. |
| 2011/0269704 A1 | 11/2011 | Seigfried |
| 2012/0010280 A1 | 1/2012 | Aleo et al. |
| 2012/0095097 A1 | 4/2012 | Tabuchi et al. |
| 2012/0238639 A1 | 9/2012 | Theisinger et al. |
| 2012/0244177 A1 | 9/2012 | Theisinger |
| 2013/0011484 A1 | 1/2013 | Bevier |
| 2013/0336557 A1 | 1/2013 | Bevier |
| 2013/0046014 A1* | 2/2013 | Theisinger .......... A61P 27/06 514/622 |
| 2013/0084250 A1 | 4/2013 | Hagedorn et al. |
| 2013/0266652 A1 | 10/2013 | Theisinger et al. |
| 2013/0303473 A1 | 11/2013 | Wilson |
| 2014/0004197 A1 | 1/2014 | Theisinger et al. |
| 2014/0100180 A1 | 4/2014 | Günther et al. |
| 2014/0140942 A1 | 5/2014 | Günther et al. |
| 2014/0186350 A1 | 7/2014 | Ghosh et al. |
| 2014/0303219 A1 | 10/2014 | Bingaman et al. |
| 2014/0369993 A1 | 12/2014 | Günther et al. |
| 2015/0045282 A1 | 2/2015 | Elsohly et al. |
| 2015/0224064 A1 | 8/2015 | Günther et al. |
| 2015/0238605 A1 | 8/2015 | Günther et al. |
| 2016/0000941 A1 | 1/2016 | Thorsten et al. |
| 2016/0101178 A1 | 4/2016 | Wilson |
| 2016/0159902 A1 | 6/2016 | Günther et al. |
| 2016/0184259 A1 | 6/2016 | Anastassov et al. |
| 2016/0243189 A1 | 8/2016 | Gu et al. |
| 2017/0020726 A1 | 1/2017 | Labombarbe et al. |
| 2017/0087100 A1 | 3/2017 | Scherer et al. |
| 2017/0087101 A1 | 3/2017 | Scherer et al. |
| 2017/0182060 A1 | 6/2017 | Wiedersberg et al. |
| 2017/0348285 A1 | 12/2017 | Hellstrom |
| 2018/0360908 A1 | 12/2018 | Beier et al. |
| 2019/0274970 A1 | 9/2019 | Günther et al. |
| 2019/0328717 A1 | 10/2019 | Günther et al. |
| 2019/0343793 A1 | 11/2019 | Günther et al. |
| 2020/0023035 A1 | 1/2020 | Löscher |
| 2020/0060987 A1 | 2/2020 | Günther et al. |
| 2020/0129543 A1 | 4/2020 | Löscher et al. |
| 2020/0188318 A1 | 6/2020 | Günther et al. |
| 2020/0206241 A1 | 7/2020 | Theisinger et al. |
| 2020/0246463 A1 | 8/2020 | Günther et al. |
| 2020/0268682 A1 | 8/2020 | Günther et al. |
| 2020/0338015 A1 | 10/2020 | Scherer et al. |
| 2021/0023166 A1 | 1/2021 | Löscher et al. |

(56) References Cited

U.S. PATENT DOCUMENTS

| | | |
|---|---|---|
| 2021/0069014 A1 | 3/2021 | Löscher et al. |
| 2021/0106558 A1 | 4/2021 | Löscher et al. |
| 2021/0121471 A1 | 4/2021 | Löscher et al. |
| 2021/0228595 A1 | 7/2021 | Löscher et al. |
| 2021/0236591 A1 | 8/2021 | Leo et al. |
| 2021/0315832 A1 | 10/2021 | Scherer et al. |
| 2021/0346313 A1 | 11/2021 | Beier et al. |
| 2022/0008397 A1 | 1/2022 | Xu et al. |
| 2022/0031844 A1 | 2/2022 | Mauden et al. |
| 2022/0079925 A1 | 3/2022 | Günther et al. |

FOREIGN PATENT DOCUMENTS

| | | | |
|---|---|---|---|
| CN | 202136470 U | 2/2012 | |
| CN | 203524843 U | 4/2014 | |
| CN | 106176937 | 12/2016 | |
| EP | 0 089 815 | 9/1983 | |
| EP | 0593552 | 4/1994 | |
| EP | 0 670 159 | 9/1995 | |
| EP | 0 965 329 | 12/1999 | |
| EP | 0 965 334 | 12/1999 | |
| EP | 1 152 749 | 11/2001 | |
| EP | 0 939 655 | 6/2002 | |
| EP | 2 110 126 | 10/2009 | |
| EP | 2 332 525 | 6/2011 | |
| EP | 2 335 735 | 6/2011 | |
| EP | 2 462 921 | 6/2012 | |
| EP | 2 802 331 | 7/2013 | |
| EP | 2 708 228 | 3/2014 | |
| JP | S5721312 A | 2/1982 | |
| JP | S6452722 | 2/1989 | |
| JP | H0764702 B2 | 7/1995 | |
| JP | 2000511157 | 8/2000 | |
| JP | 2001/158734 | 6/2001 | |
| JP | 2008/505177 | 2/2008 | |
| JP | 2011/006348 | 1/2011 | |
| JP | 2011/024841 A | 2/2011 | |
| RU | 2 111 738 C1 | 5/1998 | |
| WO | WO 92/10231 | 6/1992 | |
| WO | WO 1995/033447 | 12/1995 | |
| WO | WO 96/40052 | 12/1996 | |
| WO | WO 97/12852 | 4/1997 | |
| WO | WO 1998/005301 | 12/1998 | |
| WO | WO 00/10531 | 3/2000 | |
| WO | WO 00/024376 | 5/2000 | |
| WO | WO 00/054588 | 9/2000 | |
| WO | WO 2002/49631 A1 | 6/2002 | |
| WO | WO 2003/099258 | 12/2003 | |
| WO | WO 2005/018530 | 3/2005 | |
| WO | WO 2005/099718 | 10/2005 | |
| WO | WO 2005/099752 | 10/2005 | |
| WO | WO 2005/123035 | 12/2005 | |
| WO | WO 2006/007510 | 1/2006 | |
| WO | WO 2006/042059 | 4/2006 | |
| WO | WO 2006/048242 | 5/2006 | |
| WO | WO 2007/008666 | 1/2007 | |
| WO | WO 2007/052288 | 5/2007 | |
| WO | WO 2008/019146 | 2/2008 | |
| WO | WO 2008/060359 | 5/2008 | |
| WO | WO 2008/136034 | 11/2008 | |
| WO | WO 2009/013435 | 1/2009 | |
| WO | WO 2009/065565 | 5/2009 | |
| WO | WO 2010/062394 | 6/2010 | |
| WO | WO 2010/146536 | 12/2010 | |
| WO | WO 2011/009436 | 1/2011 | |
| WO | WO 2011/073134 | 6/2011 | |
| WO | WO 2011/113855 | 9/2011 | |
| WO | WO-2011113855 A2 * | 9/2011 | ............ A61P 27/06 |
| WO | WO 2012/007776 | 1/2012 | |
| WO | WO 2012/052418 | 4/2012 | |
| WO | WO 2012/062834 | 5/2012 | |
| WO | WO 2012/093113 | 7/2012 | |
| WO | WO 2012/121754 | 9/2012 | |
| WO | WO 2012/160179 | 11/2012 | |
| WO | WO 2012/160180 | 11/2012 | |
| WO | WO 2013/110621 | 8/2013 | |
| WO | WO 2014/041055 | 3/2014 | |
| WO | WO 2014/041071 | 3/2014 | |
| WO | WO 2014/154531 | 10/2014 | |
| WO | WO 2015/011199 | 1/2015 | |
| WO | WO 2015/053829 | 4/2015 | |
| WO | WO 2015/074137 | 5/2015 | |
| WO | WO 2016/025560 | 2/2016 | |
| WO | WO 2016/082644 | 6/2016 | |
| WO | WO 2016/108130 | 7/2016 | |
| WO | WO 2016/109531 | 7/2016 | |
| WO | WO 2017/220625 | 12/2017 | |
| WO | WO 2018/054932 | 3/2018 | |
| WO | WO 2018/055101 | 3/2018 | |
| WO | WO 2018/060282 | 4/2018 | |
| WO | WO 2018/114557 | 6/2018 | |
| WO | WO 2018/115097 | 6/2018 | |

OTHER PUBLICATIONS

Anonymous, "Highlights of Prescribing Information: Zioptan", pp. 1-11(2014) https://www.accessdata.fda.gov/drugsatfda docs/label/2015/202514s003s0041b1.pdf.

Agarwal, et al., "Semifluorinated alkane based systems for enhanced corneal penetration of poorly soluble drugs," International Journal of Pharmaceutics, 538(1-2):119-129 (2018).

Baerdemaeker "Pharmacokinetics in Obese Patients," Continuing Education in Anesthesia, Critical Care & Pain, 2004, 4:152-155.

Barata-Vallejo et al., "(Me3Si)3SiH-Mediated Intermolecular Radical Perfluoroalkylation Reactions of Olefins in Water," J. Org. Chem., 2010, 75:6141-6148.

Blackie et al., "MGD: Getting to the Root Cause of Dry Eye", Review of Optometry, 2012, pp. 1-12.

Chao, W. et al., "Report of the Inaugural Meeting of the TFOS i2 = initiating innovation Series: Targeting the Unmet Need for Dry Eye Treatment," (London, United Kingdom, Mar. 21, 2015) Accepted Manuscript, Accepted Date: Nov. 11, 2015, 94 pages.

Chemical Book, 5-Fluorouracil, available at <http://www.chemicalbook.com/ChemicalProductProperty_EN_CB8162744.htm>, accessed Mar. 7, 2014, 1 page.

Chhadv A et al., "Meibomian Gland Disease the Role of Gland Dysfunction in Dry Eye Disease," Ophthalmolrn;,:v (2017) 124(11 Supplement): S20-S26.

Gayton, J., "Etiology, Prevalence, and Treatment of Dry Eye Disease," Clinical Ophthalmology, 2009, 3:405-412.

Gerdenitsch, "Emulsions—established and promising drug carriers for parenteral administration", retrieved from Internet, date accessed: Jun. 20, 2016,URL: <http:/ipimediaworld.com/wp-content/uploads/2012/05/Pages-from-IPI-vol. 2-Issue-1-11 .pdf.>.

Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., (2017) 255(4):767-775.

Gehlsen. U., et al., "Cyclosporine A using F4H5 as liquid drug carrier is effective in treating experimental dry-eye disease," Investigative Ophthalmology & Visual Science, 2015, 56(319), Abstract Only (2 pages).

Gehlsen, U., et al., "Omega-3 Fatty Acids Using F6H8-Carrier as TopicalTherapy in Experimental Dry-Eye Disease," Investigative Ophthalmology & Visual Science, 2016, 57:417, Abstract Only (1page).

German, E.J., et al., "Reality of drop size from multi-dose eye drop bottles: is it cause for concern?" Eye, 1999, 13:93-100.

Griffin, W., "Classification of Surface-Active Agents by 'HLB'," Journal of the Society of Cosmetic Chemists, 1949, 1:311-326.

Jonas et al., "Intravitreal triamcinolone acetonide forexudative age-related macular degeneration," Br J Ophthalmol, 2003, 87:462-468.

Joussen et al., "The concept of heavy tamponades—chances and limitations," Graefes Arch Exp Ophthalmol, 2008, 246:1217-1224.

Knepp, "Stability of Nonaqueous Suspension Formulations of Plasma Derived Factor IX and Recombinant Human Alpha Interferon at Elevated Temperatures," Pharmaceutical Research, 1998, 15(7):1090-1095.

(56) References Cited

OTHER PUBLICATIONS

Lemp, M., Management of Dry Eye Disease, The American Journal of Managed Care, 2008, 14(3): S88-S101.
Lin, H. et al., "Dry eye disease: A review of diagnostic approaches and treatments," Saudi Journal of Ophthalmology, 2014, 28:173-181.
Perry, "Dry Eye Disease: Pathophysiology, Classification, and Diagnosis,"The American Journal of Managed Care, 2008, 14(3): S79-S87.
Pflugfelder et al., "The Pathophysiology of Dry Eye Disease What We Know and Future Directions for Research," Ophthalmology (2017) 124(11 Supplement): S4-S13.
Pinarci et al., "Intraocular Gas Application in the Diagnosis and Treatment of Valsalva Retiopathy in Case with Premacular Hemorrhage," Retina-Vitreus, 2009, 17(2):153-155 (Abstract Only).
Plassmann, M. et al., "Trace Analytical Methods for Semifluorinated n-Alkanes in Snow, Soil, and Air," Analytical Chemistry, 2010, 82(11):4551-4557.
Plassmann, M. et al., "Theoretical and Experimental Simulation of the Fate of Semifluorinated n-Alkanes During Snowmelt," Environmental Science & Technology, 2010, 44(17):6692-6697.
Rosca-Casian, O. et al., "Antifungal Activity of Aloe vera Leaves," Fitoterapia, 2007, 28, 219-222.
Sall, K. et al. "Two Multicenter, Randomized Studies of the Efficacy and Safety of Cyclosporine Ophthalmic Emulsion in Moderate to Severe Dry Eye Disease,"Ophthalmology, 2000, 107(4):631-639.
Sato et al., "Vitrectomy and Intraocular Lens Implantation for Cytomegalovirus Retinitis in a Patient with Acquired Immunodeficiency Syndrome," Presented by Medical Online, New Ophthalmology, 1999, 16(7): 995-998 (4 pages).
Schnetler et al., "Lipid composition of human meibum: a review," S Afr Optom, 2013, 72(2), 86-93.
Spoler et al., "Towards a New in vitro Model of Dry Eye: The ex vivo Eye Irritation Test,"Developments in Ophthalmology, 2010, 45, 93-107.
Ujiie et al., "Successful Treatment of Nail Lichen Planus with Topical Tacrolimus",Department of Deunatology, 2009.
"What is retinal vitrectomy?" Presented by: Medical Online, Obesity and Diabetes Mellitus, 2005, 4(2): 284-286 (3 pages).
Toris et al., "Update on the Mechanism of Action of Topical Prostaglandins for Intraocular Pressure Reduction," Surv Ophthalmol, 2008, 53(Suppl 1): S107-S120.
Tamura et al., "Tacrolimus is a class II low-solubility high-permeability drug: The effect of P-glycoprotein efflux on regional permeability of tacrolimus in rats," Journal of Pharmaceutical Sciences, 2002, 91(3):719-729 (Abstract Only), 1 page.
Tiffany, J.M., "Individual Variations in Human Meibomian Composition," Exp. Eye Res., 1978, 27, 289-300.
Troiano et al., "Effect of Hypotonic .4% Hyaluronic Acid Drops in Dry Eye Patients: A Cross-Study", Cornea 27(10): 1126-1130 (Abstract Only).
Ahmed, et al., "Disposition of Timolol and Inulin in the Rabbit Eye Following Corneal Versus Non-Corneal Absorption," International Journal of Pharmaceutics, 1987, 38:9-21.
Bardin et al., "Long-Range Nanometer-Scale Organization of Semifluorinated Alkane Monolayers at the Air/Water Interface," Langmuir, 2011, 27:13497-13505.
Bertilla et al., "Semifluorinated Alkanes as Stabilizing Agents of Fluorocarbon Emulsions," Springer, Tokyo, 2005, International Symposia for Life Sciences and Medicine, vol. 12, pp. 237-251.
Broniatowski, M. et al., "Langmuir Monolayers Characteristics of (Perfluorodecyl)-Alkanes," Journal of Physical Chemistry B, 2004, 108:13403-13411.
Costa Gomes et al., "Solubility of dioxygen in seven fluorinated liquids," Journal of Fluorine Chemistry, 2004, 125:1325-1329.
Davies, "Biopharmaceutical Considerations in Topical Ocular Drug Delivery," Clin. Exper. Pharmacol. Physiol., 2000, 27:558-562.
Dembinski et al., Semi-fluorinated Alkanes as Carriers for Drug Targeting in Acute Respiratory Failure, Experimental Lung Research, 2010, 36(8):499-507.
Dias et al., "Solubility of oxygen in liquid perfluorocarbon," Fluid Phase Equilibria, 2004, 222-223:325-330.
Dutescu et al., "Semifluorinated alkanes as a liquid drug carrier system for topical ocular drug delivery," European Journal of Pharmaceutics and Biopharmaceutics, 2014, 88(1):123-128, Abstract Only (2 pages).
English-language machine translation of EP0670159 (A1) issued in U.S. Appl No. 14/122,025 on Apr. 1, 2015, 10 pages.
Fischer, K.M., et al., "Effects of a topically applied 2% delta-9-tetrahydrocannabinol ophthalmic solution on intraocular pressure and aqueous humor flow rate in clinically normal dogs," American Journal of Veterinary Research, 2013, 74(2):275-280, Abstract Only (2 pages).
Freiburger Dokumentenserver (FreiDok), Albert-Ludwigs, Unversitat Feiburg im Breisgau, retrieved from the Internet, date accessed: Feb. 5, 2014, 2 pages URL: <http://www.freidok.uni-freiburg.de/volltexte/5682>.
Gehlsen. U., et al., "Cyclosporine a using F4H5 as liquid drug carrier is effective in treating experimental dry-eye disease," Investigative Ophthalmology & Visual Science, 2015, 56(7):319, Abstract Only (2 pages).
Gehlsen, U., et al., "Omega-3 Fatty Acids Using F6H8-Carrier as Topical Therapy in Experimental Dry-Eye Disease," Investigative Ophthalmology & Visual Science, 2016, 57:417, Abstract Only (1 pages).
Gopal et al., "Use of intravitreal injection of triamcinolone acetonide in the treatment of age-related macular degeneration," Indian J Ophthalmol., 2007, 55(6):431-435, (8 pages).
Hardung, H., "Semifluorierte und perfluorierte Vergindungen zur topischen und parenteralen Anwendung," 2008, 188 pages, retrieved from Internet, date accessed: Oct. 10, 2011, URL: <http://www.freidok.uni-freiburg.de/volltexte/5682/pdf/Dissertation_Hardung.pdf>.
Hardung, H., "Semifluorierte und perfluorierte Verbindungen zur topischen und parenteralen Anwendung," 2008, English Language Abstract, 2 pages, retrieved from https://freidok.uni-freiburg.de/data/5682 (retrieved on Jul. 10, 2017).
Hoerauf et al., "Combined Use of Partially Fluorinated Alkanes, Perfluorocarbon Liquids and Silicone Oil: an Experimental Study," Graefe's Archive for Clinical and Experimental Ophthalmology, 2001, 239(5):373-381.
Holm, R. et al., "A novel excipient, 1-perfluorohexyloctane shows limited utility for the oral delivery of poorly water-soluble drugs," European Journal of Pharmaceutical Sciences, 2011, 42:416-422.
International Preliminary Report on Patentability dated Apr. 23, 2013, for International Patent Application PCT/EP2011/068141, 4 Pages.
International Preliminary Report on Patentability dated Sep. 18, 2012, for International Patent Application PCT/EP2011/053949, 9 Pages.
International Preliminary Report on Patentability dated May 14, 2013, for International Patent Application PCT/EP2011/069795, 8 Pages.
International Preliminary Report on Patentability dated Jul. 10, 2013, for International Patent Application PCT/EP2012/050043, 5 Pages.
International Preliminary Report on Patentability dated Nov. 26, 2013, for International Patent Application PCT/EP2012/059787, 9 Pages.
International Preliminary Report on Patentability dated Nov. 26, 2013, for International Patent Application PCT/EP2012/059788, 8 Pages.
International Preliminary Report on Patentability dated Jul. 29, 2014, for International Application No. PCT/EP2013/051163, 7 pages.
International Preliminary Report on Patentability dated Mar. 17, 2015, for International Application No. PCT/EP2013/068882, 5 pages.
International Preliminary Report on Patentability dated Mar. 17, 2015, for International Application No. PCT/EP2013/068909, 7 pages.

(56) References Cited

OTHER PUBLICATIONS

International Preliminary Report on Patentability dated Jan. 26, 2016, for International Application No. PCT/EP2014/065840, 11 pages.
International Preliminary Report on Patentability dated Dec. 25, 2018, for International Application No. PCT/EP2017/065163, 6 pages.
International Preliminary Report on Patentability dated Mar. 26, 2019, for International Application No. PCT/EP2017/073697, 7 pages.
International Preliminary Report on Patentability dated Mar. 26, 2019, for International Application No. PCT/EP2017/074079, 7 pages.
International Preliminary Report on Patentability dated Apr. 2, 2019, for International Application No. PCT/EP2017/074545, 7 pages.
International Preliminary Report on Patentability dated Jun. 25, 2019, for International Application No. PCT/EP2017/082739, 7 pages.
International Search Report for International Application No. PCT/EP2011/053949 dated Sep. 6, 2011, 5 pages.
International Search Report for International Application No. PCT/EP2011/068141 dated Dec. 14, 2011, 2 pages.
International Search Report for International Patent Application PCT/EP2011/069795 dated Jan. 16, 2012, 3 pages.
International Search Report for International Patent Application PCT/EP2012/050043 dated Apr. 24, 2012, 2 pages.
International Search Report for International Application No. PCT/EP2012/059787 dated Dec. 5, 2012, 4 pages.
International Search Report for International Application No. PCT/EP2012/059788 dated Dec. 3, 2012, 4 pages.
International Search Report for International Application No. PCT/EP2013/051163 dated Mar. 4, 2013, 4 pages.
International Search Report for International Application No. PCT/EP2013/068882 dated Oct. 30, 2013, 4 pages.
International Search Report for International Application No. PCT/EP2013/068909 dated Dec. 5, 2013, 4 pages.
International Search Report for International Application No. PCT/EP2014/065840 dated Oct. 7, 2014, 4 pages.
International Search Report for International Application No. PCT/EP2016/073262 dated Nov. 18 2016, 5 pages.
International Search Report for International Application No. PCT/EP2016/073263 dated Dec. 23, 2016, 3 pages.
International Search Report for International Application No. PCT/EP2017/065163, dated Aug. 8, 2017, 3 pages.
International Search Report for International Application No. PCT/EP2017/073697 dated Nov. 6, 2017, 4 pages.
International Search Report for International Application No. PCT/EP2017/074079 dated Dec. 22, 2017, 4 pages.
International Search Report for International Application No. PCT/EP2017/074545 dated Nov. 28, 2017, 3 pages.
International Search Report for International Application No. PCT/EP2017/082739 dated Mar. 6, 2018, 3 pages.
International Search Report and Written Opinion for International Application No. PCT/EP2018/075974 dated Dec. 21, 2018, 8 pages.
International Search Report for International Application No. PCT/EP2017/083770 (revised version) dated Jul. 6, 2018, 4 pages.
International Search Report and Written Opinion for International Application No. PCT/EP2017/083770 dated Jul. 6, 2018, 14 pages.
Ishizaki et al., "Treatment of Diabetic Retinopathy," Forum: Complication, Practice, 2009, 26(5): 474-476 (3 pages).
JP 2000511157A, English Machine Translation of the Abstract, Description, and Claims, Espacenet, Date Accessed: Feb. 10, 2016, 15 pages.
JP56452722, English Machine Translation of the Abstract, Description, and Claims, Espacenet, Date Accessed: Feb. 10, 2016, 4 pages.
Kaercher et al., "NovaTears® as new Therapy in Dry Eye Results from three prospective, multicenter, non-interventional studies in different patient populations," TFOS Conference (Tear Film & Ocular Surface), Sep. 7-10, 2016, Montpellier, France, Poster Session II, Poster No. 60, 1 page.
Kociok, N., "Influence on Membrane-Mediated Cell Activation by Vesicles of Silicone Oil or Perfluorohexyloctane," Graefe's Archive for Clinical and Experimental Ophthalmology, 2005, 243, 345-358.
Lallemand et al., "Cyclosporine a delivery to the eye: a pharmaceutical challenge," European Journal of Pharmaceutics and Biopharmaceutics, 2003, 56(3):307-318, Abstract Only (1 page).
Mackiewicz, J. et al., "In Vivo Retinal Tolerance of Various Heavy Silicone Oils," Investigative Ophthalmology & Visual Science, 2007, 48 (4):1873-1883.
Matteucci et al., "Biocompatibility assessment of liquid artificial vitreous replacements: relevance of in vitro studies," Survey of Ophthalmology, 2007, 52(3):289-299, Abstract Only (1 page).
Meinert, H. et al., "Semifluorinated Alkanes—a New Class of Compounds with Outstanding Properties for Use in Ophthalmology," European Journal of Ophthalmology, 2000, 10 (3), 189-197.
Meinert, H. et al., "The Use of Semifluorinated Alkanes in Blood-Substitutes," Biomaterials, Artificial Cells, and Immobilization Biotechnology, 1993, 21 (5):583-595.
Messmer et al., "Semifluorierte Alkane als Therapie bei Meibomdrüsen-Dysfunktion Ergebnisse einer prospektiven, multizentrischen Beobachtungsstudie", Presentation, DOG-Kongress, Sep. 29-Oct. 2, 2016, Berlin DOG (Deutsche Ophtalmologische Gesellschaft), Poster No. PSa03-02, 1 page (German language version).
Messmer et al., "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Poster No. PSa03-02, English Translation, 6 pages.
Messmer et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Ophthalmologe, Aug. 2016 Poster No. PSa03-02, English Translation of Abstract, p. 138.
O'Rourke, M. et al., "Enhancing Delivery of Topical Ocular Drops," Cataract & Refractive Surgery Today Europe, 2016, 2 pages.
Pflugfelder et al., "Treatment of Blepharitis: Recent Clinical Trials," 2014, 12(4):273-284, Abstract Only (2 pages).
Schmutz et al., "Fluorinated Vesicles Made from Combinations of Phospholipids and Semifluorinated Alkanes. Direct Experimental Evidence of the Location of the Semifluorinated Alkane within the Bilayer," Langmuir, 2003, 19:4889-4894.
Steven, P. et al. "Semifluorinated Alkane Eye Drops for Treatment of Dry Eye Disease—A Prospective, Multicenter Noninterventional Study" Journal of Ocular Pharmacology and Therapeutics, 2015, 31(8):498-503.
Steven, P. et al. "Semifluorinated Alkane Eye Drops for Treatment of Dry Eye Disease—A Prospective, Multicenter Noninterventional Study" Investigative Ophthalmology & Visual Science, 2015, 56:4493, Abstract Only (1 page).
Steven et al., "Semifluorinated Alkane Eye Drops for Treatment of Dry Eye Disease Due to Meibomian Gland Disease," Journal of Ocular Pharmacology and Therapeutics, 2017, 33(9):1-8.
Wirta, David L. et al., "A Clinical Phase II Study to Assess Efficacy, Safety and Tolerability of Waterfree Cyclosporine Formulation for the Treatment of Dry Eye Disease," Ophthalmology, 2019, 126:792-800.
Wong et al., "Perfluorocarbons and Semifluorinated Alkanes," Seminars in Ophthalmology; vol. 15 (1), 2000, p. 25-35.
Xalatan, Latanoprost Ophthalmic Solution, 50 µg/mL Prostaglandin $F_{2\alpha}$ analogue, Product. Monograph, Jul. 21, 2014, 30 pages.
Zhang et al., "Surface micelles of semifluorinated alkanes in Langmuir-Blodgett monolayers," Phys. Chem. Chem. Phys., 2004, 6:1566-1569.
Agrahari et al., "A Comprehensive Insight on Ocular Pharmakinetics," Drug Delivery and Translation Research, vol. 6, No. 6, p. 735-754, (2016).
Blume-Peytavi et al., "A Randomized Double-blind Placebo-controlled Pilot Study to Assess the Efficacy of a 24-week Topical Treatment by Latanoprost 0.1% on Hair Growth and Pigmentation

(56) References Cited

OTHER PUBLICATIONS in Healthy Volunteers with Androgenetic Alopecia," J Am Acad Dermatol, vol. 66, No. 5, p. 794-800, (2012).

Deschamp, J. et al., "Solubility of oxygen, carbon dioxide and water in semifluorinated alkanes and in perfluorooctylbromide by molecular simulation", Jouranl of Fluorine Chemistry, Elsevier, vol. 125, No. 3, 2004.

"EvoTears—Gebrauchsanweisung," May 2015, retrieved from the Internet, date retrieved: Jun. 26, 2018, 2 pages, URL: http://video.apo-rot.de/docs/11213615.pdf.

Kerns et al., "Drug-Like Properties: Concepts, Structure Design and Methods: from ADME to Toxicity Optimization," Elsevier, Chapter 10, Section 10.4.3, 133, (2009); 2 parts.

Martin-Montanez et al., "End-of-day Dryness, Corneal Sensitivity and Blink Rate in Contact Lens Wearers," Con Lens Anterior Eye, vol. 38, No. 3, p. 148-151, (2015).

Messmer, E.M., "The Pathophysiology, Diagnosis, and Treatment of Dry Eye Disease," (2015) Deutsches Arzteblatt International, 112(5):71-82.

Novaliq GmbH Phase II Clinical Trial of Cyclasol for the Treatment of Moderate to Severe Dry Eye Disease, (online), 5 pages, (2016); retrieved on Jan. 8, 2021 from the Internet: https://www.biospace.com/article/releases/novaliq-gmbh-begins-phase-ii-clinical-trial-of-cyclasol-for-the-treatment-of-moderate-to-severe-dry-eye-disease-/.

Scherer et al., "Eyesol: A Novel Topical Ocular Drug Delivery System for Poorly Soluble Drugs," Drug Development & Delivery, vol. 13, No. 1, pp. 40-44, (2013).

"What is retinal virectomy?", Presented by: Medical Online, Obesity and Diabetes Mellitus, 2005, 4(2): 284-286 (3 pages).

Yaoxue Zhuanye Zhishi II (Editor: Jin Xiangqun), Military Medical Science Press, 1st Printing of 2nd Edition, Mar. 2009, p. 158.

Yaoxue Zhuanye Zhishi II (Editor: Jin Xiangqun), Military Medical Science Press, 1st Printing of 2nd Edition, Mar. 2009, p. 158, 3 pages (English Machine Translation).

"Latanoprost (Xalatan®),"Chemical Abstracts, CAS Registry No. 130209-82-4, retrieved from the Internet, date accessed: Mar. 21, 2022, 5 pages URL:< https://www.chemicalbook.com/CASEN_130209-82-4,htm>.

* cited by examiner

OPHTHALMIC COMPOSITIONS COMPRISING LATANOPROST FOR USE IN THE TREATMENT OF OCULAR DISEASES

CROSS-REFERENCE TO RELATED APPLICATIONS

This application is a U.S. national stage application filed under 35 U.S.C. § 371 of International Application No. PCT/EP2018/075974, filed on Sep. 25, 2018, which claims priority to, and the benefit of, European Application No. 17193364.1, filed on Sep. 27, 2017, the contents of each of which are incorporated herein by reference in their entireties.

FIELD OF THE INVENTION

The present invention relates to the field of pharmacotherapy. More specifically, it relates to the treatment of diseases and conditions affecting the eye such as glaucoma, increased intraocular pressure, ocular hypertension and/or a symptom associated therewith.

BACKGROUND OF THE INVENTION

Increased intraocular pressure is a frequent disorder of the eye which is often associated with optic nerve damage, in which case the disease is glaucoma. In the absence of optic nerve damage, the condition is referred to as ocular hypertension.

Normal intraocular pressure is usually defined as being in the range from 10 to 21 mmHg. The pressure results predominantly from balance between the production rate and the drainage rate of the aqueous humour in the eye. In addition, it is influenced by the corneal thickness and rigidity. The intraocular pressure typically fluctuates around about 15 to 16 mmHg with amplitudes of up to 6 mmHg. For example, it usually decreases in the night due to a decreased production of aqueous humour. It also responds to various physiological factors such as exercise, heart rate, respiration, fluid intake, as well as certain types of systemic or topical drugs.

The aqueous humour is produced by the ciliary bodies of the eye, from where it flows into the posterior chamber. The composition of the aqueous humour is very similar to that of blood plasma but differs from the latter by a lower protein content. Its main constituents are water (99%), electrolytes (inorganic ions to maintain the physiological pH), low amounts of albumin and β-globulins, ascorbate, glucose, lactate, and amino acids.

From the posterior chamber, the aqueous humour is distributed via the pupil of the iris into the anterior chamber of the eye. From here, it flows through the so-called trabecular meshwork, which is a spongy tissue area lined by trabeculocytes whose main function is to drain the humour into a set of tubes called Schlemm's canal, from where the humour enters the blood circulation. The humour flow from the trabecular meshwork into the Schlemm's canal occurs via two different routes: either directly via the aqueous vein to the episcleral vein, or indirectly via collector channels to the episcleral vein by intrascleral plexus. This trabecular outflow pathway accounts for the major fraction of drained aqueous humour. In addition, there exists a second major drainage pathway which is the uveoscleral outflow, which is relatively independent of the intraocular pressure and normally accounts for only 5 to 10% of the aqueous humour drainage in healthy humans.

Both in the trabecular meshwork and in the uveoscleral tissue, various prostanoid receptors have been found, which indicates that prostanoids are involved in the regulation of aqueous humour production and/or drainage and thereby influence the intraocular pressure. In the trabecular network, genes encoding the EP, FP, IP, DP and TP receptor families are expressed, whereas the EP and FP receptor families are dominant in the uveoscleral tissue (Toris et al., Surv Ophthalmol. 2008; 53, Suppl. 1, S107-S120).

Prostanoids are physiological fatty acid derivatives representing a subclass of eicosanoids. They comprise prostaglandins, prostamides, thromboxanes, and prostacyclins, all of which compounds are mediators involved in numerous physiological processes. Natural prostaglandins such as $PGF_{2\alpha}$, $PGE_2$, $PGD_2$, and $PGI_2$ exhibit a particular affinity to their respective receptors (FP, EP, DP, IP), but also have some non-selective affinity for other prostaglandin receptors (ibid.). Prostaglandins also have direct effects on matrix metalloproteinases. These are neutral proteinases expressed in the trabecular meshwork which play a role in controlling humour outflow resistance by degrading the extracellular matrix.

Several prostaglandin analogues have been found effective as topically administered medicines in reducing the intraocular pressure, such as latanoprost, bimatoprost, tafluprost, travoprost and unoprostone. By some experts, bimatoprost is understood as a prostamide rather than prostaglandin derivative.

Latanoprost, travoprost, tafluprost and probably also bimatoprost are potent and selective $PGF_{2\alpha}$ agonists. Their net effect is a reduction of intraocular pressure, which is predominantly caused by a substantial increase in aqueous humour drainage via the uveoscleral pathway. Probably they also increase the trabecular outflow to some degree.

Various eye drop formulations comprising prostaglandin analogues have been developed and are commercially available. Latanoprost and travoprost are provided as buffered, isotonised, preserved aqueous solutions in multidose bottles having a strength of 50 μg/mL (0.005%) and 40 μg/mL (0.004%), respectively. Tafluprost is available in a similar preserved formulations as well as in a non-preserved formulation in single-dose containers. The tafluprost formulations have a strength of 15 μg/mL (0.0015%) and additionally contain the surfactant, polysorbate 80. Bimatoprost is also marketed as a buffered, isotonised, and preserved aqueous solution; its strength is 0.3 mg/mL (0.03%). The strength of the commercial unoprostone formulation is 1.5 mg/mL (0.15%). It contains buffer, a preservative, an isotonising agent, and polysorbate 80.

However, preserved aqueous formulations for ophthalmic use are disadvantageous in that they are capable of producing irritancies or hypersensitivity reaction, in particular in long-term use, such as in glaucoma therapy. The most common preservative in the formulations mentioned above is benzalkonium chloride, a quaternary ammonium compound which is associated with frequent irritant toxic reactions. Non-preserved single use containers avoid this disadvantage, but they are expensive. Not only do they require a container for each single dose, but also an overfill of the formulation, which means that a substantial fraction (if not most) of the actual medicine remains in the container and is discharged as waste. Considering the drug in an eye drop which is actually administered into the eye, only a fraction of that becomes effective due to the limited volume capacity of the lacrimal sac: a significant fraction of the administered fluid volume is expelled by the blinking of the eyelids, and another fraction is taken up systemically via the nasolacrimal duct, which potentially leads to adverse drug effects.

In spite of the preservative contained in the currently available formulation of latanoprost, there have been reports of bacterial keratitis caused by microbiological contamination of the product assumingly by the patients themselves, indicating that the microbiological safety of the product is only relative.

Xalatan® (latanoprost) 0.005% eye drops solution and associated names has been approved in several EU Member States since 1996 for the reduction of elevated intraocular pressure in adult patients with open angle glaucoma and ocular hypertension. Xalatan is a sterile, isotonic, buffered aqueous solution of latanoprost at a concentration of 50 µg/mL. One drop of the aqueous solution contains approximately 1.5 µg of latanoprost and is intended for topical administration to the eye. Xalatan is supplied in a 5 mL plastic ophthalmic dispenser bottle containing 2.5 mL of Xalatan corresponding to approximately 80 drops of solution. Each mL of Xalatan contains 50 µg latanoprost, and further comprises water for injection and benzalkonium chloride as a preservative. The recommended daily dose for adults is one eye drop (corresponding to approximately 1.5 µg of latanoprost) to be administered to the affected eye(s), with an optimal effect obtained if administered in the evening.

WO2011/113855 A2 discloses pharmaceutical compositions for the treatment of increased intraocular pressure based on semifluorinated alkanes which are useful as carriers for a broad range of active ingredients. Preferred active ingredients include poorly water-soluble prostaglandin analogues such as, for example latanoprost, bimatoprost, tafluprost, travoprost and unoprostone. The compositions can be administered topically into the eye.

It is an object of the present invention to provide a novel pharmaceutical composition which is useful in a method of prevention or therapy of glaucoma, increased intraocular pressure, ocular hypertension or a symptom associated therewith, which overcomes at least one of the limitations or disadvantages associated with prior art formulations. In a specific aspect, it is an object of the invention to provide an ophthalmic composition which has the capacity to incorporate substantial amounts of poorly water-soluble drug substances useful in the management of glaucoma, increased intraocular pressure, ocular hypertension or a symptom associated therewith. Further objects of the invention will become clear on the basis of the following description, examples, and patent claims.

SUMMARY OF THE INVENTION

In a first aspect, the invention relates to a pharmaceutical composition for use in the prevention or therapy of glaucoma, increased intraocular pressure, ocular hypertension and/or a symptom associated therewith, wherein
    the composition comprises latanoprost and a liquid vehicle comprising a semifluorinated alkane; and
    the composition is administered to the eye of a subject; and
    the amount of latanoprost administered in a single dose per eye is in the range of from about 0.5 to 1.4 µg.

In a further aspect, the present invention provides a kit comprising a pharmaceutical composition for use according to the first aspect of the invention, wherein the kit comprises a container for holding the pharmaceutical composition and a drop dispenser for administering the composition.

DETAILED DESCRIPTION OF THE INVENTION

Figure 1:
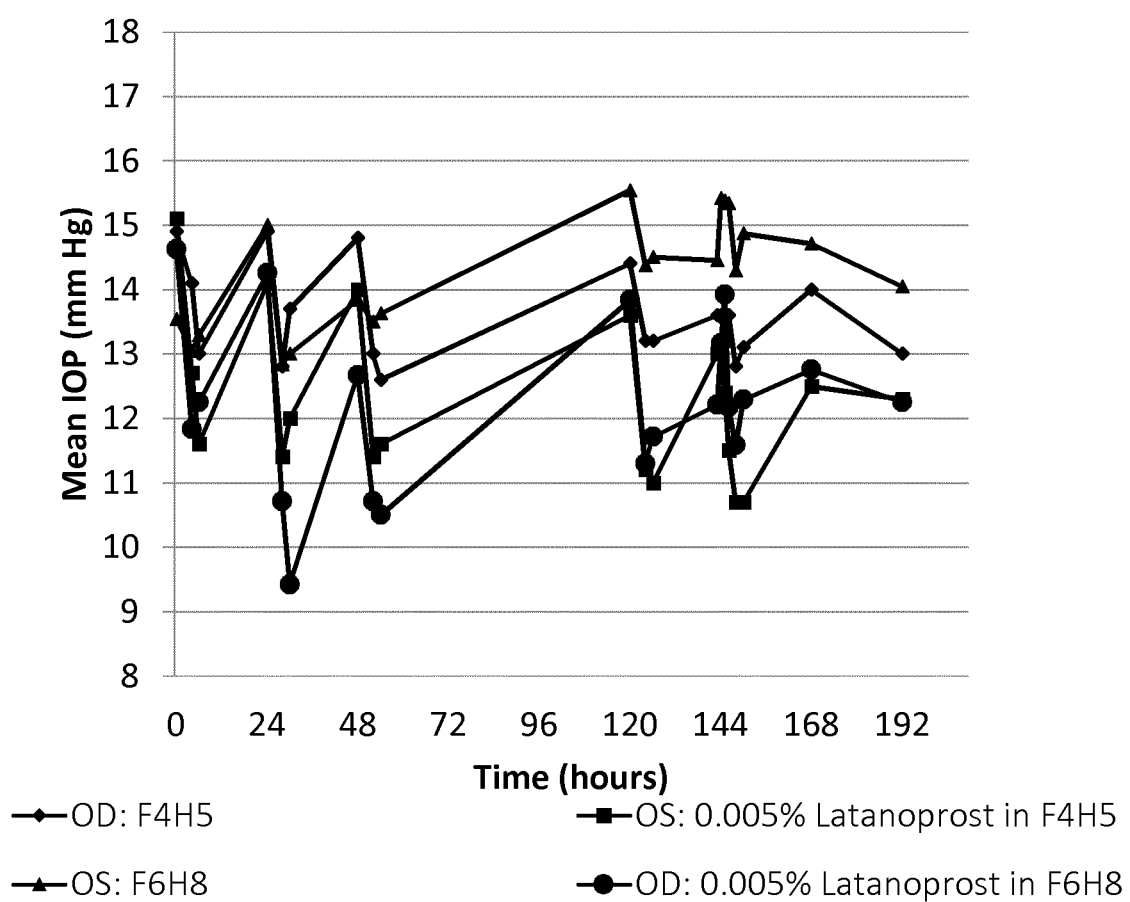
FIG. 1 shows the results of two tests of the experimental animal study (dog) further outlined below, in which the pharmacodynamics with regard to intraocular pressure (IOP) after repeated topical ocular administration of latanoprost has been investigated.

In a first aspect, the present invention relates to a pharmaceutical composition for use in the prevention or therapy of glaucoma, increased intraocular pressure, ocular hypertension and/or a symptom associated therewith, wherein
    the composition comprises latanoprost and a liquid vehicle comprising a semifluorinated alkane; and
    the composition is administered to the eye of a subject; and
    the amount of latanoprost administered in a single dose per eye is in the range of from about 0.5 to 1.4 µg.

The pharmaceutical composition according to the present invention is useful for the treatment or prevention of glaucoma and/or a symptom associated therewith, for example such as the symptoms described below. Glaucoma as understood herein is a term for eye conditions which damage the optic nerve, and which can lead to a loss of vision. The primary division in categorizing different types of glaucoma is open-angle and closed-angle (or angle-closure) glaucoma. The open angle refers to the angle where the iris meets the cornea being as wide and open as it should be, allowing the fluid from inside the eye to drain, thus relieving the internal pressure. Where this angle is narrowed or closed, pressure can build up, and eventually damage the optic nerve leading to loss of vision.

The pharmaceutical composition according to the present invention is also useful for the treatment or prevention of increased intraocular pressure (IOP) and/or a symptom associated therewith, for example such as the symptoms described below. IOP as understood herein constitutes a major risk factor for the development of glaucoma. IOP is the main cause of damage to the optic nerve and is characterized by an excessive fluid pressure within the eye, which can be due to various reasons including blockage of drainage ducts, and narrowing or closure of the angle between the iris and cornea. Elevated IOP represents a major risk factor for glaucomatous field loss. The higher the level of IOP, the greater the likelihood of optic nerve damage and visual field loss.

Furthermore, the pharmaceutical composition according to the present invention is useful for the treatment or prevention of ocular hypertension and/or a symptom associated therewith, for example such as the symptoms described below. The term ocular hypertension as understood herein denotes the presence of elevated fluid pressure inside the eye, usually, however, with no optic nerve damage or visual field loss. Elevated intraocular pressure is an important risk factor for glaucoma. For most individuals, the normal range of intraocular pressure is between 10 mmHg and 21 mmHg. Most individuals with consistently elevated intraocular pressures of greater than 21 mmHg, particularly if they have other risk factors, are therefore usually treated in an effort to prevent vision loss from glaucoma which may result from ongoing ocular hypertension. Ocular hypertension may be considered as a result of an imbalance between the fluid that enters the eye through the ciliary body and the fluid that exits the eye through the trabecular meshwork.

The composition for the use according to the present invention comprises the active ingredient latanoprost with the empirical formula $C_{26}H_{40}O_5$ and molecular weight of 432.593 g/mol (CAS Number 130209-82-4). Latanoprost is an ester prodrug that is activated to the free acid in the cornea. It is a prostaglandin F2-alpha analogue, more specifically a prostanoid selective FP receptor agonist that is believed to reduce the intraocular pressure (IOP) by increasing the outflow of aqueous humour. Studies in animals and man suggest that the main mechanism of action is increased uveoscleral outflow.

In preferred embodiments, the pharmaceutical composition for the use according to the present invention comprises about 0.005% to about 0.015% (w/v) latanoprost, more preferably about 0.008% to about 0.015% (w/v) and most preferably about 0.008% to about 0.012% (w/v) of the active compound latanoprost. In another preferred embodiment, the pharmaceutical composition for the use according to the present invention comprises about 0.010% (w/v) of the active ingredient latanoprost.

Unless otherwise indicated, the term "% (w/v)" as used throughout herein in connection with the present pharmaceutical composition denotes the amount of a component of a composition (such as, for example, latanoprost) as a weight percentage in relation to the total volume of the composition (with 'w' denoting the weight and 'v' denoting volume). For example 0.05% (w/v) may be understood as relating to 0.5 mg of a component in 1 mL of the composition, and 0.1% (w/v) would correspond to 1.0 mg of a component in 1 mL of the composition. Unless otherwise indicated, the term "% (w/w)" refers to the amount of a component of a composition as a weight percentage in relation to the total weight of the composition (with 'w' denoting weight).

The term 'about' as used herein and in reference or connection to a parameter, for example such as the concentration of latanoprost dissolved in the composition or the amount of latanoprost featured in a single dose of the composition, includes the precise value as defined, as well as any value falling within the degree of variability usually observed in measuring or determining these parameters using the standard techniques and equipment known in the art and field.

The pharmaceutical composition according to the present invention further comprises a liquid vehicle comprising a semifluorinated alkane. The active component latanoprost as described above may be dissolved or suspended, preferably dissolved in the liquid vehicle comprising a semifluorinated alkane as described below. The term "semifluorinated alkane" or "SFA" used synonymously throughout herein denotes a compound consisting of a perfluorinated hydrocarbon segment attached to a non-fluorinated hydrocarbon segment. Both segments may be branched or linear. Preferably, however, both segments are unbranched, linear segments.

In preferred embodiments, the liquid vehicle of the present pharmaceutical composition comprises a semifluorinated alkane or a mixture of two or more different semifluorinated alkanes. Preferably, however, the liquid vehicle of the present pharmaceutical composition comprises just one semifluorinated alkane.

In the present invention, preferred semifluorinated alkanes are those of the general formula (I)

$$CF_3(CF_2)_n(CH_2)_mCH_3 \qquad (I),$$

wherein the index n is an integer selected from 3 to 5, and m is an integer selected from 4 to 7.

An alternative nomenclature for the specified semifluorinated alkanes as noted in parentheses below and as may be further used herein, is based on the general formula FnHm, wherein F means the linear perfluorinated hydrocarbon segment, H means the linear non-fluorinated hydrocarbon segment and n, m is the number of carbon atoms of the respective segment. For example, F4H5 may be used to denote 1-perfluorobutyl-pentane or $CF_3(CF_2)_3$—$(CH_2)_4CH_3$ (which may be also, alternatively expressed as formula $F(CF_2)_4(CH_2)_5H)$, which has a linear perfluorinated segment F with four carbons (n=4) and a linear non-fluorinated hydrocarbon segment with five carbons (m=5). Furthermore, F6H8 may be used to denote 1-perfluorohexyl-octane or $CF_3(CF_2)_5$—$(CH_2)_7CH_3$ (which may be also, alternatively expressed as formula $F(CF_2)_6(CH_2)_8H)$, which has a linear perfluorinated segment F with six carbons (n=6) and a linear non-fluorinated hydrocarbon segment with 8 carbons (m=8).

Accordingly, said semifluorinated alkane as used in the composition of the present invention may be selected from $CF_3(CF_2)_3$—$(CH_2)_4CH_3$ (F4H5), $CF_3(CF_2)_3$—$(CH_2)_5CH_3$ (F4H6), $CF_3(CF_2)_3$—$(CH_2)_6CH_3$ (F4H7), $CF_3(CF_2)_3$—$(CH_2)_7CH_3$ (F4H8), $CF_3(CF_2)_4$—$(CH_2)_4CH_3$ (F5H5), $CF_3(CF_2)_4$—$(CH_2)_5CH_3$ (F5H6), $CF_3(CF_2)_4$—$(CH_2)_6CH_3$ (F5H7), $CF_3(CF_2)_4$—$(CH_2)_7CH_3$ (F5H8), $CF_3(CF_2)_5$—$(CH_2)_4CH_3$ (F6H5), $CF_3(CF_2)_5$—$(CH_2)_5CH_3$ (F6H6), $CF_3(CF_2)_5$—$(CH_2)_6CH_3$ (F6H7) and $CF_3(CF_2)_5$—$(CH_2)_7CH_3$ (F6H8). More preferably, said semifluorinated alkane may be selected from $CF_3(CF_2)_3$—$(CH_2)_4CH_3$ (F4H5) and $CF_3(CF_2)_5$—$(CH_2)_7CH_3$ (F6H8).

In a preferred embodiment, the pharmaceutical composition for the use according to the present invention comprises a semifluorinated alkane of formula (I) which is selected from 1-perfluorohexyl-octane ($CF_3(CF_2)_5$—$(CH_2)_7CH_3$ (F6H8)) and 1-perfluorobutyl-pentane ($CF_3(CF_2)_3$—$(CH_2)_4CH_3$ (F4H5)). In a particular preferred embodiment of the present invention, the semifluorinated alkane of formula (I) is 1-perfluorohexyl-octane ($CF_3(CF_2)_5$($CH_2)_7CH_3$, (F6H8)).

The liquid SFA's as described above are chemically and physiologically inert, colourless and stable. Their typical densities range from 1.1 to 1.7 g/cm³, and their surface tension may be as low as 19 mN/m. SFA's of the FnHm type are insoluble in water but also somewhat amphiphilic, with increasing lipophilicity correlating with an increasing size of the non-fluorinated segment.

It has been found by the inventors that SFA's are particularly suitable as carriers or vehicles in ophthalmic compositions. This is based on the fact that SFA's are unexpectedly well-tolerated by the eye, as shown in preclinical testing. This is very surprising as organic or non-aqueous solvents, perhaps with the exception of oily compounds, are typically very irritating or even highly damaging when administered to an eye.

The pharmaceutical composition or the liquid vehicle of the invention comprising "a" semifluorinated alkane is to be understood herein, as comprising at least one semifluorinated alkane of Formula (I) as described above. Optionally, however, the composition or liquid vehicle may comprise more than one, for example, a mixture of two or more semifluorinated alkanes of Formula (I), i.e. of any one of the semifluorinated alkane species as described above.

In yet further embodiment, the liquid vehicle of the present pharmaceutical composition may consist of a semifluorinated alkane of Formula (I) as specified above. In this context, the term "a" semifluorinated alkane is to be understood as at least one semifluorinated alkane, but may also include the option of more than one, or a plurality of semifluorinated alkane compounds. Accordingly, in one embodiment, the liquid vehicle may consist of more than one semifluorinated alkane of Formula (I) as specified above.

As used herein, the term "consists" and related terms "consisting" or "consist" is to be understood as meaning that no other features, other than those prefaced by the term are present. In the context of compositions, if any other constituent or component is present in the composition other than those prefaced by such term, then it is present only in trace or residual amounts such as to confer no technical advantage or relevance in respect of the object of the invention, such as may be further understood by the term 'essentially" or "substantially" used in conjunction with these terms (e.g. 'essentially consisting of"). It is to be understood that isomeric or olefinic impurities that originate from synthesis of semifluorinated alkanes and that are present in only trace or residual amounts as these cannot be quantitatively removed upon purification and that do not confer any technical advantage or relevance in respect of the object of the present invention, do fall under the above definition of such other constituent or component. In contrast, the term 'comprising" or related terms "comprises" or "comprise" in the context of the present compositions, is to be understood as meaning that other features, other than those prefaced by the term may be present in the composition.

In further embodiment, the liquid vehicle of the present pharmaceutical composition as defined in any of the previous embodiments described above, preferably comprises a semifluorinated alkane or, optionally, a mixture of semifluorinated alkanes in an amount of at least 70% (w/w), 75% (w/w), 85% (w/w), 90% (w/w), 95% (w/w), 98% (w/w), 98.5% (w/w), 99% (w/w), 99.5% (w/w), 99.8% (w/w) or at least 99.9% (w/w), with respect to the total weight of the liquid vehicle. In a preferred embodiment of the present invention, the liquid vehicle comprises at least 97.5% (w/w) of a semifluorinated alkane with respect to the total weight of the liquid vehicle.

The term "% (w/w)" as used herein and unless indicated otherwise refers to the amount of a component of a composition as a weight percentage in relation to the total weight of the liquid vehicle of the present pharmaceutical composition (with 'w' denoting weight).

In yet further embodiments of the present invention, the liquid vehicle preferably comprises a semifluorinated alkane or, optionally, a mixture of semifluorinated alkanes as described above in an amount of from about 90% (w/w) to about 99.9% (w/w), more preferably from about 95% (w/w) or 97% (w/w) or 97.5% (w/w) to about 99.5% (w/w) with respect to the total weight of the liquid vehicle. In a most preferred embodiment of the present invention, the liquid vehicle comprises a semifluorinated alkane in an amount of from about 97.5% (w/w) to about 99.5% (w/w) with respect to the total weight of the liquid vehicle.

In further embodiments, the present pharmaceutical composition, more specifically, the liquid vehicle of the present pharmaceutical composition may further comprise a solubilising agent. The term "solubilizing agent" as used herein denotes a compound or combination of compounds that enhances or facilitates the solubility of the active component latanoprost in the chosen liquid vehicle comprising a semifluorinated alkane as described above. In preferred embodiments, as already mentioned above, latanoprost is completely dissolved in the liquid vehicle comprising a semifluorinated alkane and optionally a solubilizing agent.

The solubilizing agent, that may be optionally comprised by the liquid vehicle of the present pharmaceutical composition, may preferably be present in an amount of up to 3% (w/w), or preferably of up to 2.5% (w/w) with respect to the total weight of the liquid vehicle. In a preferred embodiment, the liquid vehicle comprises a solubilising agent in amounts as low as up to 1% (w/w), preferably up to 0.5% (w/w) with respect to the total weight of the liquid vehicle. In another preferred embodiment, the liquid vehicle further comprises a solubilising agent in an amount of from about 2.5% to 0.5% (w/w), preferably of from about 1% to 0.5% (w/w) with respect to the weight of the liquid vehicle.

In some embodiments, the solubilizing agent may be a liquid excipient such as, for example, an organic cosolvent and/or an oil selected from glyceride oils, liquid waxes and liquid paraffin, or an organic solvent exhibiting a high degree of biocompatibility.

Examples of potentially useful liquid excipients comprise oily excipients which may be used in combination with one or more SFA's and include triglyceride oils, mineral oil, medium chain triglycerides (MCT), oily fatty acids isopropyl myristate, oily fatty alcohols, esters of sorbitol and fatty acids, oily sucrose esters or any other substance which is physiologically tolerated by the eye. In one of the preferred embodiment, the liquid vehicle comprises a solubilizing agent in form of a liquid excipient. In this case it is even more preferred that the liquid excipient is MCT, preferably at a concentration of up to 3% (w/w), more preferably of up to 2.5% (w/w) with regard to the total weight of the liquid vehicle.

Further examples of potentially useful solubilizing agents as used herein are organic solvents. Preferred organic solvents include glycerol, propylene glycol, polyethylene glycol and ethanol. In a preferred embodiment, the liquid vehicle of the present composition may comprise diethylene glycol monoethyl ether (DEGEE) as the solubilizing agent, preferably in an amount of up to 1.5% (w/w), more preferably of up to 1% (w/w) with regard to the weight of the liquid vehicle of the present pharmaceutical composition.

In yet further preferred embodiment, the liquid vehicle of the present pharmaceutical composition may comprise ethanol as the solubilizing agent, preferably in an amount of up to 1% (w/w), more preferably of up to 0.8% (w/w) and most preferred of up to 0.5% (w/w) with regard to the weight of the liquid vehicle of the present pharmaceutical composition.

Accordingly, in preferred embodiments, the liquid vehicle of the present pharmaceutical composition further comprises a solubilizing agent. Preferably the solubilising agent is selected from ethanol, MCT and DEGEE.

The pharmaceutical composition for the use according to the present invention may or may not also comprise further excipients, such as, for example, preservatives, more specifically preservatives and/or surfactants. In a preferred embodiment, however, the pharmaceutical composition according to the present invention is substantially free of a preservative.

In a preferred embodiment, the pharmaceutical composition for use according to the present invention is substantially free of water. As understood herein, the term 'substantially free', or alternatively 'essentially free' in reference to a composition constituent refers to the presence of said constituent in no more than trace amounts and that if present in trace amounts the constituent provides no technical contribution to the composition.

In a yet further preferred embodiment, the pharmaceutical composition for the use according to the present invention is substantially free of water and of a preservative.

In a particularly preferred embodiment, the pharmaceutical composition for the use according to the present invention comprises latanoprost dissolved in a liquid vehicle essentially consisting of at least 99% (w/w) of 1-perfluorobutyl-pentane ($CF_3(CF_2)_3$—$(CH_2)_4CH_3$ (F4H5)) or 1-perfluorohexyl-octane ($CF_3(CF_2)_5$—$(CH_2)_7CH_3$ (F6H8)) and up to 1% (w/w) of ethanol with respect to the total weight of the liquid vehicle.

In a further preferred embodiment, the pharmaceutical composition for the use according to the present invention comprises latanoprost dissolved in a liquid vehicle essentially consisting of at least 99.5% (w/w) of 1-perfluorobutyl-pentane ($CF_3(CF_2)_3$—$(CH_2)_4CH_3$ (F4H5)) or 1-perfluorohexyl-octane ($CF_3(CF_2)_5$—$(CH_2)_7CH_3$ (F6H8)) and up to 0.5% (w/w) of ethanol with respect to the total weight of the liquid vehicle.

In a further preferred embodiment, the pharmaceutical composition for the use according to the present invention comprises latanoprost dissolved in a liquid vehicle essentially consisting of at least 99.5% (w/w) of 1-perfluorohexyl-octane ($CF_3(CF_2)_5$—$(CH_2)_7CH_3$ (F6H8)) and up to 0.5% (w/w) of ethanol with respect to the total weight of the liquid vehicle.

In a more preferred embodiment, the pharmaceutical composition for the use according to the present invention essentially consists of latanoprost dissolved in a liquid vehicle essentially consisting of at least 99.5% (w/w) of 1-perfluorohexyl-octane ($CF_3(CF_2)_5$—$(CH_2)_7CH_3$ (F6H8)) and up to 0.5% (w/w) of ethanol with respect to the total weight of the liquid vehicle.

As outlined above, the composition for the use of the present invention is preferably provided as a clear solution, wherein the latanoprost is fully dissolved in the chosen liquid vehicle. Furthermore, the composition for the use according to the present invention is preferably provided in sterile form.

The pharmaceutical composition for use according to the present invention comprising latanoprost and a liquid vehicle comprising a semifluorinated alkane may be administered topically to the eye of a subject or may be administered to the eye of a subject by subconjunctival injection. In a preferred embodiment, however, the pharmaceutical composition for use according to the present invention is administered topically to the eye of the subject.

The term "administered topically" as used herein comprises all possible methods of administration which allow the present liquid pharmaceutical composition to be brought in contact with a surface of the eye of a subject. Typically, the present pharmaceutical composition may be administered in the form of a single drop or a plurality of drops or droplets to an eye of a subject. The drop may be administered to the surface of the eye, preferably to any surface region or tissue of the eye that is accessible to topical administration or instillation, for example to the cornea or conjunctiva. The drop or droplet of the composition may be instilled directly onto a surface of the eye, such as the corneal surface of the eye, or alternatively into a space i.e. sac or pocket formed by gently pulling down of the lower eyelid of an eye.

The term "subconjunctival injection" as used herein means any form of injection of the pharmaceutical composition of the present invention below the conjunctiva of the eye of a subject. This may comprise injection of the pharmaceutical composition by suitable syringes. The term subconjunctivital injection may also comprise injection by a medical device or insert to be inserted below the conjunctiva, e.g. through an generated opening in the conjunctiva.

As used herein, the term 'administration to an eye' or 'per eye' refers to the administration of a given dose, e.g. a single dose, of a pharmaceutical composition for the use according to the invention to an individual eye of a subject. The therapy of the ocular diseases as described herein, namely glaucoma, increased intraocular pressure, ocular hypertension and/or a symptom associated therewith, however, should be understood as being not limited to the treatment of a single eye in a subject, but as being also inclusive of a therapy involving the administration of the composition for the use according to the present invention to each i.e. both eyes of a subject which are affected by said diseases.

The term "subject" as used herein means a human or animal, preferably however a human, suffering from, diagnosed with or endangered by developing glaucoma, increased intraocular pressure, ocular hypertension and/or a symptom associated therewith.

The pharmaceutical composition for use according to the present invention comprising latanoprost and a liquid vehicle comprising a semifluorinated alkane is further characterized in that the amount of latanoprost administered in a single dose per eye is in the range of from about 0.5 to 1.4 µg. In a preferred embodiment, however, the amount of latanoprost administered in a single dose per eye is in the range of from about 0.7 to 1.4 µg, preferably from about 1.0 to 1.2 µg, even more preferably about 1.1 µg.

The pharmaceutical composition for use according to the present invention forms small droplets (drops). In a preferred embodiment of the present invention, the volume of the composition administered in a single dose per eye, herein referred to as composition "target dose volume per eye", is in the range of about 6 to 28 µl, more preferably in the range of about 6 to 24 µl, and most preferably in the range of about 6 to 15 µl, when administered from a suitable drop dispenser. In another preferred embodiment of the present invention, the pharmaceutical composition for the use according to the present invention has a composition target dose volume per eye in the range of about 8 to 15 µl, preferably in the range of about 9 to 14 µl, most preferably in the range of about 10 to 12 µl. In a most preferred embodiment of the present invention, the composition target dose volume per eye is about 11 µl. This further distinguishes the composition of the present invention from the aqueous latanoprost compositions such as, for example, Xalatan, that are characterized by droplet sizes of about 30 µl.

Accordingly, in preferred embodiments, the pharmaceutical composition for use in the prevention or therapy of glaucoma, increased intraocular pressure, ocular hypertension and/or a symptom associated therewith, wherein the composition comprises latanoprost and a liquid vehicle comprising a semifluorinated alkane; and wherein the composition is administered to the eye of a subject; and wherein the amount of latanoprost administered in a single dose per eye is in the range of from about 0.5 to 1.4 µg, the amount of latanoprost to be administered in a single dose per eye is provided in a defined volume of the pharmaceutical composition (hereinafter referred to as "composition target dose volume per eye"). In further preferred embodiments, the composition target dose volume per eye (containing the amount of latanoprost to be administered in a single dose per eye) is 30 µl or below, preferably lower than 25 µl, more preferably lower than 15 µl.

In a preferred embodiment of the present invention, the pharmaceutical composition for use according to the present invention comprises about 0.005% to 0.015% (w/v) latanoprost and a liquid vehicle comprising a semifluorinated alkane; the composition is administered to the eye of a subject; and the amount of latanoprost administered in a single dose per eye is in the range of from about 1.0 to 1.2 µg.

In another preferred embodiment of the present invention, the pharmaceutical composition for use according to the present invention comprises about 0.008% to 0.015% (w/v) latanoprost and a liquid vehicle comprising a semifluorinated alkane; the composition is administered to the eye of a subject; and the amount of latanoprost administered in a single dose per eye is in the range of from about 1.0 to 1.2 µg.

In another preferred embodiment of the present invention, the pharmaceutical composition for use according to the present invention comprises about 0.008% to 0.012% (w/v) latanoprost and a liquid vehicle comprising a semifluorinated alkane; the composition is administered to the eye of a subject; and the amount of latanoprost administered in a single dose per eye is in the range of from about 1.0 to 1.2 µg.

In a particularly preferred embodiment, the pharmaceutical composition for the use according to the present invention comprises about 0.008% to about 0.012% (w/v) latanoprost, and the latanoprost administered in a single dose per eye is about 1.1 µg.

In another preferred embodiment, the pharmaceutical composition for use according to the present invention comprises about 0.010% (w/v) latanoprost and a liquid vehicle comprising a semifluorinated alkane, wherein the composition is administered to the eye of a subject, and wherein the latanoprost administered in a single dose per eye is about 1.1 µg and the target does volume per eye is about 11 µl.

In a most preferred embodiment, the pharmaceutical composition for use according to the present invention comprises latanoprost and a liquid vehicle comprising a semifluorinated alkane, wherein the composition is administered to the eye of a subject, wherein the amount of latanoprost administered in a single dose per eye is in the range of from about 1.0 to about 1.2 µg and the target dose volume per eye is in the range of from about 6 to 24 µl, preferably from about 6 to 15 µl, more preferably from about 8 to 15 µl, even more preferably from about 10 to 12 µl, most preferably 11 µl.

Accordingly, in preferred embodiments, the pharmaceutical composition for use according to the present invention is administered once daily. In further preferred embodiments, the single dose of the pharmaceutical composition for use according to the present invention is administered as one single drop to an eye of a subject.

Figure 2:
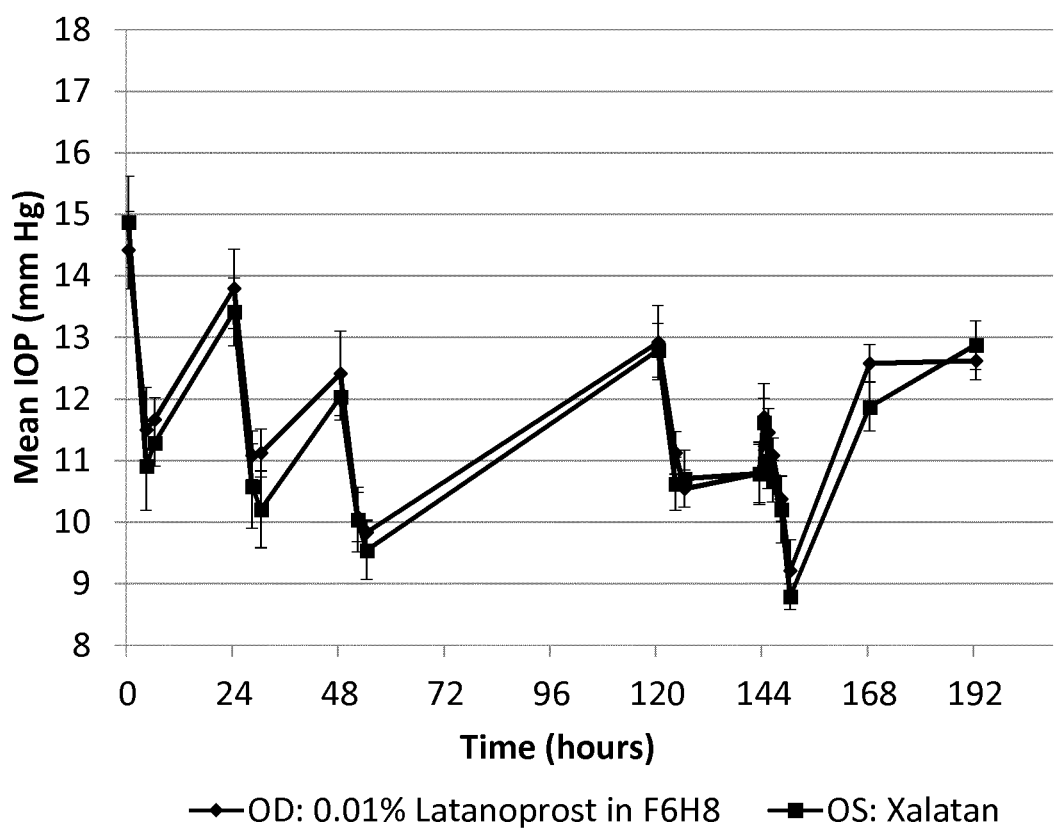
FIG. 2 shows the results of a head to head comparison of a composition comprising latanoprost in F6H8 administered to the right eye (OD) of a test animal versus Xalatan® administered to the left eye (OS) of the same test animal.

It has been surprisingly found, that the presence of an SFA as described above as a constituent of the liquid vehicle allows for the preparation of the present pharmaceutical composition with beneficial combinations of single dose amounts of latanoprost with composition target dose volumes which are advantageous when compared to known aqueous compositions as described above. Specifically, it is possible to achieve a decrease of the intraocular pressure which is comparable to the decrease achieved by administering the commercial composition Xalatan, which is characterised by a target dose per eye of 1.5 µg and a target dose volume per eye of 30 µl. As shown in FIG. 2, a composition having for example a target dose per eye of 1.1 µg shows a decrease of the intraocular pressure comparable to that of Xalatan. Further, another advantage of the pharmaceutical composition for the use according to the present invention is that the composition can be administered in considerably lower target dose volumes, compared to the target dose volume of Xalatan.

As an example, in preferred embodiments, the pharmaceutical composition for use according to the present invention is characterized by the comparable low volume of composition to be administered in a single dose per eye (composition target dose volume), such as about 8 µl to about 15 µl, preferably about 10 µl to about 12 µl, more preferably about 11 µl.

Furthermore, one complication associated with the administration of aqueous compositions with a significantly larger drop size is that usually only fraction of the amount of aqueous composition administered topically to the surface of the eye actually stays there. In many cases, some of the comparatively large volume of the aqueous composition immediately leaks from the surface of the eye and is often wiped off. Therefore, a surplus of composition is often necessary to ensure that the therapeutically effective amount of latanoprost actually reaches the eye.

Based on this, the pharmaceutical composition for the use of the present invention allows for a significant reduction of droplet size and target dose volume associated therewith and therefore, as outlined above for a significant reduction of the total daily dose of latanoprost administered for use in the treatment of glaucoma, increased intraocular pressure, ocular hypertension and/or a symptom associated therewith.

In a second aspect, the present invention provides for a kit comprising a pharmaceutical composition according to the first aspect of the invention, namely for use in the prevention or therapy of glaucoma, increased intraocular pressure, ocular hypertension and/or a symptom associated therewith, wherein the composition comprises latanoprost and a liquid vehicle comprising a semifluorinated alkane; and
the composition is administered to the eye of a subject; and
the amount of latanoprost administered in a single dose per eye is in the range of from about 0.5 to 1.4 µg, wherein the kit comprises a container for holding the pharmaceutical composition and a drop dispenser for administering the composition.

It is to be understood that all embodiments as described in detail above in connection with the pharmaceutical composition for use according to the first aspect of the invention may be comprised by the kit according to this second aspect of the invention.

As understood herein, the drop dispenser may be a dispenser or applicator means which may be mounted, fixed or connected to the container for holding the pharmaceutical composition. Preferably, the drop dispenser is adapted for dispensing a single dose in the form of a single drop of the pharmaceutical composition according to the first aspect of the invention. More preferably, the drop dispenser is adapted for dispensing a single dose of about 8 µl to about 15 µl volume, preferably of about 10 µl to about 12 µl volume or even more preferably is adapted for dispensing a single dose of about 11 µl volume.

The container for holding the pharmaceutical composition as understood herein is preferably of a volume which may hold a single dose, but more preferably of a volume which may hold multiple or a plurality of doses of the composition.

The container and/or the drop dispenser preferably may be manufactured from a thermoplastic material or polymer. In a one embodiment, the container and/or the drop dispenser is manufactured from a thermoplastic material selected from polyethylene and polypropylene.

In one particular embodiment, the drop dispenser is manufactured from a polyethylene material, preferably selected from low density polyethylene and high density polyethylene, and more preferably is manufactured from a high-density polyethylene. In another embodiment, the container is manufactured from a polypropylene or polyethylene material, and more preferably is manufactured from polypropylene.

Preferably, the container has a volume, or an interior space which is at least partially filled with the pharmaceutical composition for use according to the invention. In a further embodiment, the ratio of the volume of the pharmaceutical composition in the container to the total volume of the container is between 0.4 and 0.7. The total volume of the container, as understood herein refers to the total interior volume formed by the interior dimensions of the container. The volume of the pharmaceutical composition in the container refers to the fill volume, i.e. the volume of the pharmaceutical composition held in the container. For example, in a kit comprising a container with a total volume of 3.0 ml, it is preferred that the container holds a volume of 2.0 ml of a pharmaceutical composition according to the invention. Here, the ratio of the volume of the pharmaceutical composition in the container to the total volume of the container would be about 0.7.

Such kits as provided in accordance with these embodiments may improve storage and dispensability (i.e., ease and consistency in dispensing) of the pharmaceutical composition according to the first aspect of the present invention.

In a third aspect, the present invention refers to a method of treating or preventing glaucoma, increased intraocular pressure, ocular hypertension and/or a symptom associated therewith, the method comprising administering to an eye of a subject, preferably to a human with glaucoma, increased intraocular pressure, ocular hypertension or a symptom associated therewith, a composition comprising latanoprost and a liquid vehicle comprising a semifluorinated alkane, wherein the amount of latanoprost administered in a single dose per eye is about 0.5 to 1.4 µg, and wherein said method is therapeutically effective in treating glaucoma, increased intraocular pressure, ocular hypertension and/or a symptom associated therewith.

In a fourth aspect, the present invention provides for a pharmaceutical composition for use in a method of prevention or therapy of glaucoma, increased intraocular pressure, ocular hypertension and/or a symptom associated therewith, wherein the composition comprises latanoprost and a liquid vehicle comprising a semifluorinated alkane, wherein said composition is therapeutically effective in treating or preventing glaucoma, increased intraocular pressure, ocular hypertension and/or a symptom associated therewith when administered in a single dose per eye of about 0.5 to 1.4 µg latanoprost.

In a fifth aspect, the present invention relates to a method of reducing the total daily amount of latanoprost administered to a human for the treatment of glaucoma, increased intraocular pressure, ocular hypertension and/or a symptom associated therewith comprising administering once daily to an eye of said human a composition comprising latanoprost and a liquid vehicle comprising a semifluorinated alkane, preferably comprising latanoprost dissolved in an SFA, wherein the amount of latanoprost administered in a single dose per eye is about 0.5 to 1.4 µg and wherein said method reduces the amount of latanoprost per total daily dose by about 67% to 7% and the amount of latanoprost administered in a single dose per eye is at least as therapeutically effective in treating glaucoma, increased intraocular pressure, ocular hypertension and/or a symptom associated therewith as compared to daily administration of a single drop per eye of an aqueous solution comprising 0.005% (w/v) latanoprost.

In a preferred embodiment of the method according to this fifth aspect of the present invention, the single drop of said composition has a drop volume of about 11 µl and the single drop of said 0.005% (w/v) latanoprost aqueous solution has a drop volume of about 30 µl.

In a further preferred embodiment of the method according to this fifth aspect of the present invention, the systemic exposure to latanoprost is reduced as compared to daily administration of a single drop of 0.005% (w/v) latanoprost aqueous solution.

In a yet further preferred embodiment of the method according to this fifth aspect of the present invention, one or more adverse effects are reduced as compared to daily administration of a single drop of 0.005% (w/v) latanoprost aqueous solution. The term "adverse effects" as used herein means, according to the general meaning, an undesired harmful effect resulting from a medication, in this particular case resulting from topical ocular administration of latanoprost, such as, for example, blurred vision, burning and stinging, conjunctival hyperemia, foreign body sensation, itching, increased (brown) pigmentation of the iris causing (heterochromia), lengthening and thickening of the eyelashes, punctate epithelial keratopathy, cold or upper respiratory tract infections, flu-like syndrome, dry eyes, excessive tearing, eye pain, lid crusting, lid edema, lid erythema (hyperemia), lid pain, photophobia, chest pain, allergic skin reactions, arthralgia, back pain, myalgia, asthma, herpes keratitis, iritis, keratitis, retinal artery embolus, retinal detachment, toxic epidermal necrolysis, uveitis, vitreous hemorrhage from diabetic retinopathy, and/or keratoconus.

In a sixth aspect, the present invention provides for a method of reducing the total daily amount of latanoprost administered to a human for the treatment of glaucoma, increased intraocular pressure, ocular hypertension and/or a symptom associated therewith, the method comprising administering once daily to an eye of a human with glaucoma, increased intraocular pressure, ocular hypertension and/or a symptom associated therewith a single drop of a composition comprising about 0.01% (w/v) latanoprost dissolved in F6H8 or F4H5, wherein said composition is substantially free of water and is substantially free of preservative, wherein the amount of latanoprost administered in a single dose per eye is about 1.1 µg, and wherein said method reduces the amount of latanoprost per total daily dose by about 27% and wherein said method is at least as therapeutically effective in treating glaucoma, increased intraocular pressure, ocular hypertension and/or a symptom associated therewith as compared to a once daily administration of a single drop per eye of an aqueous solution comprising 0.005% (w/v) latanoprost.

It is to be understood that all embodiments as described in detail above in connection with the pharmaceutical compositions for use according to the first aspect of the invention may be applied to the methods according to the third to seventh aspect of the present invention.

Detailed Description of the Figures

FIG. 1 shows the results of the experimental animal study (dog) further outlined below, in which the pharmacodynamics with regard to intraocular pressure (IOP) after repeated topical ocular administration of latanoprost (0.005% (w/v)) in either F4H5 or F6H8 versus the corresponding semifluorinated alkanes alone has been investigated. The graphs show the development of the mean intraocular pressure (IOP) in mmHg over time.

FIG. 2 shows the results of the head to head comparison of a composition comprising latanoprost (0.01% (w/v)) in F6H8 administered to the right eye (OD) of a test animal versus Xalatan® administered to the left eye (OS) of the same test animal as further outlined below. The graphs shows the development of the mean intraocular pressure (IOP) in mmHg over time.

The following list of numbered items are embodiments comprised by the present invention:

1. A pharmaceutical composition for use in the prevention or therapy of glaucoma, increased intraocular pressure, ocular hypertension and/or a symptom associated therewith, wherein
   the composition comprises latanoprost and a liquid vehicle comprising a semifluorinated alkane; and
   the composition is administered to the eye of a subject; and
   the amount of latanoprost administered in a single dose per eye is in the range of from about 0.5 to 1.4 µg.
2. The composition for the use according to item 1, wherein the semifluorinated alkane is selected from F6H8 and F4H5.
3. The composition for the use according to item 1 or 2, wherein the semifluorinated alkane is F6H8.
4. The composition for use according to any one of the preceding items, wherein the composition is administered to the eye of a subject topically or by subconjunctival injection.
5. The composition for use according to any one of the preceding items, wherein the composition is administered topically to the eye of a subject.
6. The composition for use according to any one of items 1 to 4, wherein the composition is administered to the eye of a subject by subconjunctival injection.
7. The composition for the use according to any one of the preceding items, wherein the composition further comprises a solubilising agent.
8. The composition for the use according to item 7, wherein solubilising agent is selected from ethanol, MCT and DEGEE.
9. The composition for the use according to item 7 or 8, wherein the solubilising agent is comprised in an amount of up to 2.5% (w/w) with respect to the total weight of the liquid vehicle.
10. The composition for the use according to any one of items 7 to 9, wherein the solubilising agent is ethanol.
11. The composition for the use according to item 10, wherein the amount of ethanol is up to 0.5% (w/w) with respect to the total weight of the liquid vehicle.
12. The composition for use according to any one of the preceding items, wherein the composition is substantially free of water and of a preservative.
13. The composition for use according to any one of the preceding items, wherein the composition target dose volume per eye is from about 8 to 15 µl.
14. The composition for the use according to any one of the preceding items, wherein the composition target dose volume per eye is from about 10 to 12 µl.
15. The composition for the use according to any one of the preceding items, wherein the composition comprises about 0.005 to 0.015% (w/v), preferably about 0.008 to 0.012% (w/v) latanoprost.
16. The composition for the use according to any one of the preceding items, wherein the amount of latanoprost administered in a single dose per eye is in the range of from about 1.0 to 1.2 µg.
17. The composition for the use according to any one of the preceding items, wherein the composition comprises about 0.01% (w/v) latanoprost, and wherein the latanoprost administered in a single dose per eye is about 1.1 µg and wherein the composition target dose volume per eye is about 11 µl.
18. The pharmaceutical composition for use according to any one of the preceding items, wherein the composition essentially consists of latanoprost dissolved in a liquid vehicle essentially consisting of at least 99% (w/w) of 1-perfluorobutyl-pentane ($CF_3(CF_2)_3$—$(CH_2)_4CH_3$ (F4H5)) and/or 1-perfluorohexyl-octane ($CF_3(CF_2)_5$—$(CH_2)_7CH_3$ (F6H8)) and up to 1% (w/w) of ethanol with respect to the total weight of the liquid vehicle.
19. The composition for the use according to any one of the preceding items, wherein the composition is administered once daily.
20. The pharmaceutical composition for use according to any one of the preceding items, wherein the single dose of the composition is administered as one single drop to an eye of a subject.
21. A pharmaceutical composition for use in a method of prevention or therapy of glaucoma, increased intraocular pressure, ocular hypertension or a symptom associated therewith, wherein the composition comprises latanoprost dissolved in a liquid vehicle comprising a semifluorinated alkane and wherein the amount of latanoprost administered in a single dose per eye is in the range between about 0.5 to about 1.4 µg.
22. The composition for use according to item 21, wherein the composition target dose volume per eye is from about 8 to about 15 µl.
23. The composition for the use according to item 21 or 22, wherein the composition comprises about 0.005 to 0.015% (w/v), preferably about 0.008 to 0.012% (w/v) latanoprost.
24. The composition for the use according to any one of items 21 to 23, wherein the latanoprost administered in a single dose per eye is about 1.0 to 1.2 µg.
25. The composition for the use according to any of one of items 21 to 24, wherein the composition target dose volume per eye is from about 10 to 12 µl.
26. The composition for the use according to any of items 21 to 25, wherein the composition further comprises a solubilising agent, preferably selected from ethanol, MCT and DEGEE.
27. The composition for the use according to item 26, wherein the solubilising agent is comprised in an amount of at most 2.5% (w/w) with respect to the total weight of the liquid vehicle.
28. The composition for the use according to item 26, wherein the solubilising agent is ethanol.

29. The composition for the use according to item 28, wherein the amount of ethanol is at most 1.0% (w/w), preferably at most 0.5% (w/w) with respect to the total weight of the liquid vehicle.
30. The composition for the use according to any one of items 21 to 29, wherein the composition comprises about 0.01% (w/v) latanoprost; the latanoprost administered in a single dose per eye is about 1.1 µg and the target dose volume per eye is about 11 µl.
31. The composition for the use according to any one of items 21 to 30, wherein the SFA is one selected from F6H8 and F4H5.
32. The composition for the use according to item 31, wherein the SFA is F6H8.
33. The composition for the use according to any one of items 21 to 32, wherein the composition is administered once daily.
34. The composition for the use according to any one of items 21 to 33, wherein the composition is substantially free of water and of preservative.
35. A kit comprising a pharmaceutical composition for use according to any one of the preceding items, wherein the kit comprises a container for holding the pharmaceutical composition and a drop dispenser for administering the composition.
36. The kit according to item 35, wherein the container for holding the pharmaceutical composition and the drop dispenser are adapted for administering about 8 to 15 µl volume of the composition per drop, preferably 10 to 12 µl volume of the composition per drop, more preferably 11 µl volume of the composition per drop.
37. A method of treating glaucoma, increased intraocular pressure, ocular hypertension or a symptom associated therewith, the method comprising administering to an eye of a human with glaucoma, increased intraocular pressure, ocular hypertension or a symptom associated therewith, a composition comprising latanoprost and a liquid vehicle comprising a semifluorinated alkane, wherein the latanoprost is preferably dissolved in the liquid vehicle, wherein the amount of latanoprost administered in a single dose per eye is about 0.5 to about 1.4 µg, and wherein said method is therapeutically effective in treating glaucoma, increased intraocular pressure, ocular hypertension or a symptom associated therewith.
38. The method according to item 37, wherein the composition target dose volume per eye is from about 8 to about 15 µl.
39. The method according to item 37 or 38, wherein the composition comprises about 0.005 to 0.015% (w/v), preferably about 0.008 to 0.012% (w/v) latanoprost.
40. The method according to any one of items 37 to 39, wherein the latanoprost administered in a single dose per eye is about 1.0 to 1.2 µg.
41. The method according to any one of items 37 to 40, wherein the composition target dose volume per eye is from about 10 to about 12 µl, preferably about 11 µl.
42. The method according to any one of items 37 to 41, wherein the composition further comprises a solubilising agent, preferably selected from ethanol, MCT and DEGEE.
43. The method according to any one of items 37 to 42, wherein the solubilising agent is comprised in an amount of at most 2.5% (w/w) with respect to the total weight of the liquid vehicle.
44. The method according to item 42, wherein the solubilising agent is ethanol.
45. The method according to item 44, wherein the amount of ethanol is at most 1% (w/w), preferably at most 0.5% (w/w) with respect to the total weight of the liquid vehicle.
46. The method according to any one of items 37 to 45, wherein the composition comprises about 0.01% w/v latanoprost; the latanoprost administered in a single dose per eye is about 1.1 µg and the target dose volume per eye is about 11 µl.
47. The method according to any of items 37 to 46, wherein the semifluorinated alkane is one selected from F6H8 and F4H5.
48. The method according to item 47, wherein the semifluorinated alkane is F6H8.
49. The method according to any one of items 37 to 48, wherein the composition is administered once daily.
50. The method according to any one of items 37 to 49, wherein the composition is substantially free of water and of preservative.
51. The method according to item 37, wherein said composition further comprises up to about 1% (w/w) ethanol.
52. The method according to item 37, wherein said composition consists of latanoprost dissolved in a solution of about 99% (w/w) F4H5 or F6H8 and about 1% (w/w) ethanol.
53. The method according to item 37, wherein said composition consists of latanoprost dissolved in a solution of at least about 99% (w/w) F4H5 or F6H8 and up to about 1% (w/w) ethanol.
54. The method according to item 37, wherein said composition further comprises up to about 0.5% (w/w) ethanol.
55. The method according to item 37, wherein said composition consists of latanoprost dissolved in a solution of about 99.5% (w/w) F4H5 or F6H8 and about 0.5% (w/w) ethanol.
56. The method according to item 37, wherein said composition consists of latanoprost dissolved in a solution of at least about 99.5% (w/w) F4H5 or F6H8 and up to about 0.5% (w/w) ethanol.
57. A pharmaceutical composition for use in a method of prevention or therapy of glaucoma, increased intraocular pressure, ocular hypertension or a symptom associated therewith, wherein the composition comprises latanoprost and a liquid vehicle comprising a semifluorinated alkane, wherein the latanoprost is preferably dissolved in the semifluorinated alkane, wherein said composition is therapeutically effective in treating or preventing glaucoma, increased intraocular pressure, ocular hypertension or a symptom associated thereof when administered in a single dose per eye of about 0.5 to 1.4 µg latanoprost.
58. The composition for the use according to item 57, wherein the composition target dose volume per eye is from 8 to 15 µl.
59. The composition for the use according to item 57, wherein the composition comprises about 0.005 to 0.015% (w/v), preferably about 0.008 to 0.012% (w/v) latanoprost.
60. The composition for the use according to item 57, wherein the latanoprost administered in a single dose per eye is about 1.0 to 1.2 µg.
61. The composition for the use according to item 57, wherein the composition target dose volume per eye is from about 10 to 12 µl.
62. The composition for the use according to item 57, wherein said composition comprises up to about 0.5% (w/w) ethanol.

63. The composition for use according to item 57, wherein said composition consists of latanoprost dissolved in a solution of about 99.5% (w/w) F4H5 or F6H8 and about 0.5% (w/w) ethanol.
64. The composition for use according to item 57, wherein said composition consists of latanoprost dissolved in a solution of at least about 99.5% (w/w) F4H5 or F6H8 and up to about 0.5% (w/w) ethanol.
65. The composition for use according to item 57, wherein said composition further comprises up to about 1% (w/w) ethanol.
66. The composition for use according to item 57, wherein said composition consists of the latanoprost dissolved in a solution of about 99% (w/w) F4H5 or F6H8 and about 1% (w/w) ethanol.
67. The composition for use according to item 57, wherein said composition consists of latanoprost dissolved in a solution of at least about 99% (w/w) F4H5 or F6H8 and up to about 1% (w/w) ethanol.
68. The composition for use according to item 57, wherein said latanoprost is comprised in a concentration of about 0.008% to 0.012% (w/v) and said single dose per eye is about 1.0 to 1.2 µg, preferably 1.1 µg latanoprost and wherein said composition is substantially free of water and is substantially free of a preservative.
69. The composition for the use according to item 68, wherein said composition comprises up to about 0.5% (w/w) ethanol.
70. The composition for use according to item 68, wherein said composition consists of latanoprost dissolved in a solution of about 99.5% (w/w) F4H5 or F6H8 and about 0.5% (w/w) ethanol.
71. The composition for use according to item 68, wherein said composition consists of latanoprost dissolved in a solution of at least about 99.5% (w/w) F4H5 or F6H8 and up to about 0.5% (w/w) ethanol.
72. The composition for use according to item 68, wherein said composition further comprises up to about 1% (w/w) ethanol.
73. The composition for use according to item 68, wherein said composition consists of the latanoprost dissolved in a solution of about 99% (w/w) F4H5 or F6H8 and about 1% (w/w) ethanol.
74. The composition for use according to item 68, wherein said composition consists of latanoprost dissolved in a solution of at least about 99% (w/w) F4H5 or F6H8 and up to about 1% (w/w) ethanol.
75. A method of reducing the total daily amount of latanoprost administered to a human for the treatment of glaucoma, increased intraocular pressure, ocular hypertension or a symptom associated therewith comprising administering once daily to an eye of said human a composition comprising latanoprost dissolved in a liquid vehicle comprising a semifluorinated alkane, wherein the amount of latanoprost administered in a single dose per eye is about 0.5 to 1.4 µg and wherein said method reduces the amount of latanoprost per total daily dose by about 67 to 7% and is at least as therapeutically effective in treating glaucoma, increased intraocular pressure, ocular hypertension or a symptom associated therewith as compared to daily administration of a single drop per eye of a 0.005% (w/v) latanoprost aqueous solution.
76. The method of reducing the total daily amount of latanoprost administered to a human for the treatment of glaucoma, increased intraocular pressure, ocular hypertension or a symptom associated therewith according to item 75, wherein the single drop of said composition has a drop volume of about 11 µl and the single drop of said 0.005% (w/v) latanoprost aqueous solution has a drop volume of about 30 µl.
77. The method of reducing the total daily amount of latanoprost administered to a human for the treatment of glaucoma, increased intraocular pressure, ocular hypertension or a symptom associated therewith according to item 75 or 76, wherein the systemic exposure to latanoprost is reduced as compared to daily administration of a single drop of 0.005% (w/v) latanoprost aqueous solution.
78. The method of reducing the total daily amount of latanoprost administered to a human for the treatment of glaucoma, increased intraocular pressure, ocular hypertension or a symptom associated therewith according to any one of items 75 to 77, wherein one or more adverse effects are reduced as compared to daily administration of a single drop of 0.005% (w/v) latanoprost aqueous solution.
79. The method of reducing the total daily amount of latanoprost administered to a human for the treatment of glaucoma, increased intraocular pressure, ocular hypertension or a symptom associated therewith according to item 78, wherein the one or more adverse effects are selected from the group of adverse effects consisting of blurred vision, burning and stinging, conjunctival hyperemia, foreign body sensation, itching, increased (brown) pigmentation of the iris causing (heterochromia), lengthening and thickening of the eyelashes, punctate epithelial keratopathy, cold or upper respiratory tract infections, flu-like syndrome, dry eyes, excessive tearing, eye pain, lid crusting, lid edema, lid erythema (hyperemia), lid pain, photophobia, chest pain, allergic skin reactions, arthralgia, back pain, myalgia, asthma, herpes keratitis, iritis, keratitis, retinal artery embolus, retinal detachment, toxic epidermal necrolysis, uveitis, vitreous hemorrhage from diabetic retinopathy, and keratoconus.
80. A method of reducing the total daily amount of latanoprost administered to a human for the treatment of glaucoma, increased intraocular pressure, ocular hypertension or a symptom associated therewith, the method comprising administering once daily to an eye of a human with glaucoma, increased intraocular pressure, ocular hypertension or a symptom associated therewith a single drop of a composition comprising about 0.01% (w/v) latanoprost dissolved in F6H8 or F4H5, wherein said composition is substantially free of water and is substantially free of preservative, wherein the amount of latanoprost administered in a single dose per eye is about 1.1 µg latanoprost, and wherein said method reduces the amount of latanoprost per total daily dose by about 27% and is at least as therapeutically effective in treating glaucoma, increased intraocular pressure, ocular hypertension or a symptom associated therewith as compared to a once daily administration of a single drop per eye of a 0.005% (w/v) latanoprost aqueous solution.

The following examples serve to illustrate the invention, however, should not to be understood as restricting the scope of the invention.

EXAMPLES

Example 1

The study as described below was carried out in order to assess the pharmacodynamics of latanoprost (intraocular pressure, IOP) following repeated topical ocular doses of latanoprost in respectively perfluorobutylpentane (F4H5)

and perfluorohexyloctane (F6H8) in normotensive dogs and to evaluate the pharmacokinetics of latanoprost acid in aqueous humor. The dog is a suitable species for evaluating ocular distribution and pharmacodynamics of prostaglandin analogs; this model can also provide quantitative pharmacokinetic data.

Study Setup:

The animals were selected for participation in the study based on overall health, body weight, results of ophthalmic examinations, response to IOP challenge, and the following criteria:
- healthy, normal ocular surface;
- no invasive ocular procedures for at least one month prior to the study;
- particularly procedures involving the cornea or ocular anterior segment in general;
- no topical or systemic corticosteroid treatment for at least one month;
- washout from prior topical ocular study medication commensurate with the typical washout period used for clinical studies (at least one week)

Study Design:

The study was performed according to the plan as summarized in Table 1 below. The topical ocular dose (11 or 30 μl, respectively) was administered to the central or superior part of the cornea via a micropipette and allowed to spread across the surface of the eye. After the dose was administered, the eye was allowed to close naturally. Each animal was restrained for approximately one minute to prevent rubbing of the eyes.

composition comprising latanoprost 0.005% (w/v) in F6H8 containing 0.5% (w/w) ethanol: 1,625 g ethanol (Seccosolv, Merck, max 0.01% $H_2O$) are mixed with 324.3 g F6H8 (99.888%, from Lomapharm, GmbH) to yield to a solution having 0.5% (w/w) ethanol. Then 2.558 mg latanoprost (99.5% from Yonsung, South Korea) are dissolved in 50 mL of the F6H8 solution containing 0.5% (w/w) ethanol to yield to a solution comprising 0.005% (w/v) latanoprost.

The compositions administered in the prestudies and in each phase are herein described:

Prestudy 1:
OD: 0.005% (w/v) Latanoprost Solution;
OS: Phosphate-buffered saline (PBS)

Prestudy 2:
OD: 0.005% (w/v) Latanoprost Solution;
OS: 0.005% (w/v) Latanoprost Solution;

Phase 1:
OD: Perfluorobutylpentane containing 0.5% (w/w) Ethanol
OS: PBS

Phase 2:
OD: 0.00125% (w/v) Latanoprost in Perfluorobutylpentane containing 0.5% (w/w) Ethanol
OS: Perfluorobutylpentane containing 0.5% (w/w) Ethanol Phase 3:
OD: Perfluorobutylpentane containing 0.5% (w/w) Ethanol
OS: 0.0025% (w/v) Latanoprost in Perfluorobutylpentane containing 0.5% (w/w) Ethanol

TABLE 1

| Phase/Group[a] | Number of Female Animals | Topical Ocular Dose Regime OD | Topical Ocular Dose Regime OS | Target Dose Level (μg/eye) OD | Target Dose Level (μg/eye) OS | Target Dose Volume (μL/eye) | Dose frequency |
|---|---|---|---|---|---|---|---|
| Prestudy 1 | 14 | Latanoprost | PBS | 1.5 | 0 | 30 | Once |
| Prestudy 2 | 14 | Latanoprost | Latanoprost | 1.5 | 1.5 | 30 | Once |
| 1/1 | 8 | A (F4H5) | PBS | 0 | 0 | 11 | QD for 7 d |
| 2/1 | 8 | B (0.00125%) | B (F4H5) | 0.138 | 0 | 11 | QD for 7 d |
| 3/1 | 8 | C (F4H5) | C (0.0025%) | 0 | 0.275 | 11 | QD for 7 d |
| 4/1 | 8 | D (F4H5) | D (0.005%) | 0 | 0.550 | 11 | QD for 7 d |
| 5/1 | 8 | E (0.005%) | E (F6H8) | 0.550 | 0 | 11 | QD for 7 d |
| 6/1 | 8 | G (F6H8) | PBS | 0 | 0 | 11 | QD for 7 d |
| 7/1 | 8 | F (0.005%) | F (F4H5) | 1.50 | 0 | 30 | QD for 7 d |
| 8/1 | 8 | H (0.01%) | H (F6H8) | 1.10 | 0 | 11 | QD for 7 d |
| 9/1 | 8 | I (F6H8) | I (0.015%) | 0 | 1.65 | 11 | QD for 7 d |
| 10/1 | 8 | J (0.01% F6H8 + MCT) | J (F6H8 + MCT) | 1.10 | 0 | 11 | QD for 7 d |
| 11/1 | 8 | K (F6H8 + MCT) | K (PBS) | 0 | 0 | 11 | QD for 7 d |
| 12/1 | 8 | L (0.01% Latanoprost in F6H8) | L (Xalatan ®) | 1.10 | 1.50 | 11/30 | QD for 7 d |
| 13/1 (PK,[b]) | 8 | M (0.01% Latanoprost in F6H8) | L (0.01% Latanoprost in F6H8) | 1.10 | 1.10 | 11 | QD for 7 d |
| 14/1 | 8 | N (F6H8 + DEGEE) | N (0.01% F6H8 + DEGEE) | 0 | 1.10 | 11 | QD for 7 d | d Days
IOP Intraocular pressure
OD Right eye
OS Left eye
PBS Phosphate buffered saline
QD Once daily
[a]There was at least a 7-day washout period between each phase, including prestudy.
[b]collected from 4 eyes/time point.

The pharmaceutical compositions used in the Phases 1 to 14 were prepared by dissolving latanoprost in the liquid vehicle comprising a semifluorinated alkane.

As an example of the production of the compositions used in the 14 phases, herein described is the preparation of the Phase 4:
OD: Perfluorobutylpentane containing 0.5% (w/w) Ethanol
OS: 0.005% (w/v) Latanoprost in Perfluorobutylpentane containing 0.5% (w/w) Ethanol Phase 5:
OD: 0.005% (w/v) Latanoprost in Perfluorohexyloctane containing 0.5% (w/w) Ethanol
OS: Perfluorohexyloctane containing 0.5% (w/w) Ethanol
Phase 6:
OD: Perfluorohexyloctane containing 0.5% (w/w) Ethanol
OS: PBS
Phase 7:
OD: 0.005% (w/v) Latanoprost in Perfluorobutylpentane containing 0.5% (w/w) Ethanol
OS: Perfluorobutylpentane containing 0.5% (w/w) Ethanol
Phase 8:
OD: 0.010% (w/v) Latanoprost in Perfluorohexyloctane containing 0.5% (w/w) Ethanol
OS: Perfluorohexyloctane containing 0.5% (w/w) Ethanol
Phase 9:
OD: Perfluorohexyloctane containing 0.5% (w/w) Ethanol
OS: 0.015% (w/v) Latanoprost in Perfluorohexyloctane containing 0.5% (w/w) Ethanol
Phase 10:
OD: 0.010% (w/v) Latanoprost in Perfluorohexyloctane containing 2.5% (w/w) medium-chain triglycerides (MCT)
OS: Perfluorohexyloctane containing 2.5% (w/w) MCT
Phase 11:
OD: Perfluorohexyloctane containing 2.5% (w/w) MCT
OS: PBS
Phase 12:
OD: 0.010% (w/v) Latanoprost in Perfluorohexyloctane containing 0.5% (w/w) Ethanol
OS: Xalatan [0.005% (w/v) Latanoprost Solution]
Phase 13:
OD: 0.010% (w/v) Latanoprost in Perfluorohexyloctane containing 0.5% (w/w) Ethanol
OS: 0.010% (w/v) Latanoprost in Perfluorohexyloctane containing 0.5% (w/w) Ethanol
Phase 14:
OD: perfluorohexyloctane containing 1.0% (w/w) 2-(2-Ethoxyethoxy) ethanol (DEGEE)
OS: 0.010% (w/w) Latanoprost in Perfluorohexyloctane containing
1.0% (w/w) 2-(2-Ethoxyethoxy) ethanol Two weeks prior to phase 1, in the intraocular efficacy prestudy no. 1 (see Table 1, Prestudy 1), a single dose of 30 µl of latanoprost ophthalmic solution 0.005% (w/v) was administered to the right eye (OD) and phosphate buffered saline (PBS) to the left eye (OS) of each animal for an intraocular efficacy challenge. The resulting IOP was measured using a tonometer TonoVet at −1, 0 (immediately predose), 1, 2, 4, 6, 24 and 48 hours postdose.

One week prior to phase 1, in the prestudy intraocular efficacy challenge no. 2 (see Table 1, Prestudy 2), a single dose of 30 µl of latanoprost ophthalmic solution 0.005% (w/v) was administered to both eyes of each animal. The corresponding IOP was measured using a TonoVet at −1, 0 (immediately predose), 4 and 6 hours postdose.

Prestudies 1 and 2 were performed in order to evaluate the IOP response (Prestudy 1) and the similarities between the eyes (prestudy 2). The animals which were responsive to the IOP and showed similarities between the eyes in the response to the treatment were selected for the 14 phases of the study as outlined in Table 1. Additional criteria for the selection of the animals were a baseline intraocular pressure of at least 13 mmHg, a response of at least 15% decrease in IOP from baseline following treatment with Xalatan® and the behavior of the animals during IOP measurement.

After the two prestudy efficacy phases, the animals were subjected to the 14 phases of the study as described in Table 1. The intraocular pressure measurements during the phases 1 to 14, were made on days 1, 2, 3 and 6 at 0 (immediately predose), 4 and 6 hours postdose as well as on day 7 at −1, 0 (immediately predose), 1, 2, 4, 6, 24, and 48 hours postdose. Three readings/eye were taken using a TonoVet.

Ocular irritation scoring during the phases 1 to 14 were made at predose (up to 2 days prior to dosing), on days 1, 2, 3 and 6 at 0 (immediately predose), 4 and 6 hours postdose following IOP measurements; on day 7 at 0 (immediately predose), 4, 6, 24 and 48 hours postdose following IOP measurements. Both eyes were scored/graded using a modified Hackett-McDonald scale technique following IOP measurements. Sporadic findings of irritation were present during dosing sessions; however, there were no apparent differences between dose groups or phases.

Study Analysis:

As shown in FIG. 1 the administration of Latanoprost solution in respectively F4H5 and in F6H8 resulted in a decrease of the intraocular pressure. The latanoprost solutions in F4H5 and F6H8 further comprised 0.5% (w/w) of ethanol.

FIG. 2 refers to phase 12 of the study as outlined in Table 1 and shows the head to head comparison of a composition comprising Latanoprost in F6H8 versus Xalatan®, in which the administration of a solution of Latanoprost in F6H8, having a target dose level of 1.1 µg/eye and a target dose volume of 11 µl/eye, shows a decrease of the IOP comparable to that achieved by instilling Xalatan® having a target dose level of 1.5 µg/eye and a target dose volume of 30 µl/eye. The experimental data shows that by using a composition according to the present invention it is possible to achieve a decrease of the IOP comparable to that of the gold standard Xalatan®, even with using a lower target dose of the active ingredient. Further, the lower target dose can be administered in a volume of for example 11 µl, i.e. in a volume considerably lower than 30 µl, thus allowing a reduction of the amount of composition which is expelled or which it taken up systemically.

The invention claimed is:

1. A method for the prevention or therapy of increased intraocular pressure, comprising administering a pharmaceutical composition comprising latanoprost and a liquid vehicle comprising a semifluorinated alkane to a patient in need thereof, wherein:
  the composition is administered to the eye of a subject;
  the composition comprises about 0.01% (w/v) latanoprost, and about 0.5% (w/w) ethanol, with respect to the total weight of the liquid vehicle;
  the amount of latanoprost administered in a single dose per eye is in the range of from about 1.0 to 1.2 µg;
  the composition target dose volume per eye is from about 10 to 12 µl; and
  the semifluorinated alkane is F6H8.

2. The method according to claim 1, wherein the composition consists of about 0.01% (w/v) latanoprost dissolved in a solution of about 99.5% (w/w) F6H8 and about 0.5% (w/w) ethanol, with respect to the total of the liquid vehicle.

3. The method according to claim 1, wherein the composition is administered topically to the eye of a subject.

4. The method according to claim 1, wherein the composition is substantially free of water and of a preservative.

5. The method according to claim 1, wherein the composition target dose volume per eye is about 11 µl.

6. The method according to claim 1, wherein the amount of latanoprost administered in a single dose per eye is in the range of from about 1.0 to 1.1 µg.

7. The method according to claim 1, wherein the latanoprost administered in a single dose per eye is about 1.1 μg and wherein the composition target dose volume per eye is about 11 μl.

8. The method according to claim 1, wherein the composition comprises about 0.01% (w/v) latanoprost dissolved in a liquid vehicle comprising at least 97.5% (w/w) of 1-perfluorohexyl-octane ($CF_3(CF_2)_5$—$(CH_2)_7CH_3$ (F6H8)) and about 0.5% (w/w) ethanol, with respect to the total weight of the liquid vehicle.

9. The method according to claim 1, wherein the composition is administered once daily.

10. The method according to claim 1, wherein the composition consists of about 0.01% (w/v) latanoprost dissolved in a solution of about 99.5% (w/w) F6H8 and about 0.5% (w/w) ethanol, with respect to the total weight of the liquid vehicle, and wherein the latanoprost administered in a single dose per eye is about 1.1 μg and wherein the composition target dose volume per eye is about 11 μl and wherein the composition is effective in treating increased intraocular pressure.

11. The method according to claim 10, wherein the method is effective in reducing the total daily dose by about 27%, as compared to a once daily administration of a single drop per eye of an aqueous solution comprising 0.005% (w/v) latanoprost.

12. The method according to claim 1, wherein the composition comprises about 0.01% (w/v) latanoprost dissolved in a solution of at least 97.5% (w/w) F6H8 and about 0.5% (w/w) ethanol, with respect to the total weight of the liquid vehicle, and wherein the latanoprost administered in a single dose per eye is about 1.1 μg and wherein the composition target dose volume per eye is about 11 μl and wherein the composition is effective in treating increased intraocular pressure.

13. The method according to claim 12, wherein the method is effective in reducing the total daily dose by about 27%, as compared to a once daily administration of a single drop per eye of an aqueous solution comprising 0.005% (w/v) latanoprost.

* * * * *

UNITED STATES PATENT AND TRADEMARK OFFICE
CERTIFICATE OF CORRECTION

| | |
|---|---|
| PATENT NO. | : 11,723,861 B2 |
| APPLICATION NO. | : 16/651298 |
| DATED | : August 15, 2023 |
| INVENTOR(S) | : Günther et al. |

It is certified that error appears in the above-identified patent and that said Letters Patent is hereby corrected as shown below:

In the Claims

Claim 2, Column 24, Line 58, "with respect to the total of the liquid vehicle" should be changed to "with respect to the total weight of the liquid vehicle"

Signed and Sealed this
Third Day of September, 2024

Katherine Kelly Vidal
*Director of the United States Patent and Trademark Office*